(12) United States Patent
Wilson et al.

(10) Patent No.: US 9,701,957 B2
(45) Date of Patent: Jul. 11, 2017

(54) REAGENT HOLDER, AND KITS CONTAINING SAME

(75) Inventors: Kerry Wilson, Elkhart, IN (US); Kalyan Handique, Ypsilanti, MI (US); Sundaresh N. Brahmasandra, Ann Arbor, MI (US); Jeff Williams, Chelsea, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 795 days.

(21) Appl. No.: 12/218,416

(22) Filed: Jul. 14, 2008

(65) Prior Publication Data

US 2009/0129978 A1  May 21, 2009

Related U.S. Application Data

(60) Provisional application No. 60/959,437, filed on Jul. 13, 2007.

(51) Int. Cl.
*B01L 3/14* (2006.01)
*C12N 15/10* (2006.01)
(Continued)

(52) U.S. Cl.
CPC .......... *C12N 15/1013* (2013.01); *C07H 1/08* (2013.01); *C12Q 1/6813* (2013.01)

(58) Field of Classification Search
USPC .............. 422/61, 63, 65, 99, 100; 435/975
See application file for complete search history.

(56) References Cited

U.S. PATENT DOCUMENTS 1,434,314 A   10/1922  Raich
1,616,419 A    2/1927  Wilson
(Continued)

FOREIGN PATENT DOCUMENTS

CA   2294819    1/1999
DE   19929734   12/1999
(Continued)

OTHER PUBLICATIONS

BioTek Instruments, Inc., "Precision XS Microplate Sample Processor", Product Description, Copyright 2009 by BioTek Instruments, Inc., [retrieved on Aug. 13, 2009[. Retrieved from the Internet: <URL: http://www.biotek.com/products/liquid_handling/precision_xs_microplate_sample_processor.html>, 11 pages.
(Continued)

*Primary Examiner* — Sharon Pregler
(74) *Attorney, Agent, or Firm* — Knobbe, Martens, Olson & Bear, LLP

(57) ABSTRACT

A holder for reagents, such as may be used for transporting the reagents and for carrying out processing operations on biological samples with the reagents. The holders typically hold reagents for amplifying polynucleotides extracted from the samples. The holder comprises a connecting member; a process tube affixed to the connecting member and having an aperture located in the connecting member; at least one socket, located in the connecting member, and configured to accept a pipette tip; two or more reagent tubes disposed on the underside of the connecting member, each having an inlet aperture located in the connecting member; and one or more receptacles, located in the connecting member and each being configured to receive a reagent tube. Also described are reagent tubes configured with stellated shaped patterns, on their bottom interior surfaces, configured to facilitate complete or near-complete withdrawal of fluid from the tube, via a pipette tip.

9 Claims, 15 Drawing Sheets

(51) Int. Cl.
*C12Q 1/68* (2006.01)
*C07H 1/08* (2006.01)

(56) References Cited

U.S. PATENT DOCUMENTS

| | | |
|---|---|---|
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Teraski et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,892 A | 4/1990 | Plumb |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |

(56) References Cited

U.S. PATENT DOCUMENTS

| | | |
|---|---|---|
| 5,646,039 A | 7/1997 | Northrup et al. |
| 5,647,994 A | 7/1997 | Tuunanen et al. |
| 5,651,839 A | 7/1997 | Rauf |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A * | 5/2000 | Fassbind et al. ............. 422/102 |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk, Jr. |

(56) References Cited

U.S. PATENT DOCUMENTS

| | | | |
|---|---|---|---|
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Lines et al. |
| 6,238,626 B1 | 5/2001 | Higuchi et al. |
| 6,251,343 B1 | 6/2001 | Dubrow et al. |
| 6,254,826 B1* | 7/2001 | Acosta et al. ............... 422/100 |
| 6,259,635 B1 | 7/2001 | Torelli et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-Sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-Sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-Sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-Sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1* | 8/2003 | Tajima ...................... 422/102 |
| 6,613,211 B1 | 9/2003 | Mccormick et al. |
| 6,613,512 B1 | 9/2003 | Kopf-Sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |

(56) References Cited

U.S. PATENT DOCUMENTS

| | | |
|---|---|---|
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-Sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair et al. |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| 7,727,371 B2 | 6/2010 | Kennedy et al. |
| 7,727,477 B2 | 6/2010 | Boronkay et al. |
| 7,744,817 B2 | 6/2010 | Bui |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 | 8/2011 | Handique et al. |
| 8,088,616 B2 | 1/2012 | Handique |
| 8,105,783 B2 | 1/2012 | Handique |
| 8,133,671 B2 | 3/2012 | Williams et al. |
| 8,182,763 B2 | 5/2012 | Duffy et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |

(56) References Cited

U.S. PATENT DOCUMENTS

| | | |
|---|---|---|
| 8,470,586 B2 | 6/2013 | Wu et al. |
| 8,473,104 B2 | 6/2013 | Handique et al. |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schmebri |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014238 A1 | 1/2004 | Krug et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086956 A1 | 5/2004 | Bachur |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1* | 10/2005 | Lloyd et al. .............. 435/6 |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0207944 A1 | 9/2006 | Siddiqi |
| 2006/0210435 A1 | 9/2006 | Alavie et al. |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |

(56) References Cited

U.S. PATENT DOCUMENTS

| | | |
|---|---|---|
| 2009/0221059 A1 | 9/2009 | Williams et al. |
| 2009/0223925 A1 | 9/2009 | Morse et al. |
| 2010/0009351 A1 | 1/2010 | Brahmasandra et al. |
| 2010/0173393 A1 | 7/2010 | Handique et al. |
| 2011/0008825 A1 | 1/2011 | Ingber et al. |
| 2011/0027151 A1 | 2/2011 | Handique et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0160826 A1 | 6/2012 | Handique |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0101990 A1 | 4/2013 | Handique et al. |
| 2013/0164832 A1 | 6/2013 | Ganesan et al. |

FOREIGN PATENT DOCUMENTS

| | | |
|---|---|---|
| EP | 0766256 | 4/1997 |
| EP | 2372367 A1 | 10/2011 |
| FR | 2672301 | 8/1992 |
| FR | 2795426 | 12/2000 |
| JP | 58212921 A | 12/1983 |
| JP | H 03181853 | 8/1991 |
| JP | H07-290706 | 11/1995 |
| JP | H 08122336 A | 5/1996 |
| JP | H 11503315 | 3/1999 |
| JP | H 11316226 | 11/1999 |
| JP | 2001-509437 | 7/2001 |
| JP | 2001-515216 | 9/2001 |
| JP | A-2001-527220 | 12/2001 |
| JP | 2002-215241 | 7/2002 |
| JP | A-2003-500674 | 1/2003 |
| JP | 2005010179 | 1/2005 |
| JP | 2005-514718 | 5/2005 |
| JP | A-2005-204661 | 8/2005 |
| JP | 2005-291954 A | 10/2005 |
| JP | 2005291954 A | 10/2005 |
| JP | 2007178328 A | 7/2007 |
| WO | WO 88/06633 | 9/1988 |
| WO | WO 90/12350 | 10/1990 |
| WO | WO 92/05443 | 4/1992 |
| WO | WO 97/05492 | 2/1997 |
| WO | WO 98/00231 | 1/1998 |
| WO | WO 98/22625 | 5/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 2004/007081 | 1/2004 |
| WO | WO 2004/055522 | 7/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2007/044917 | 4/2007 |
| WO | WO 2007/050327 | 5/2007 |
| WO | WO 2008/030914 | 3/2008 |
| WO | WO 2008/060604 | 5/2008 |
| WO | WO 2009/012185 | 1/2009 |
| WO | WO 2010/118541 | 10/2010 |

OTHER PUBLICATIONS

Bioron GmbH, "Bioron: Net—Advanced Products for Molecular Biology and PCR Diagnostics: OPT-reagent", Product Description, Copyright by Bioron GmbH, Ludwigshafen, Germany [retrieved on Aug. 13, 2009]. Retrieved from the Internet: <URL: http://www.bioron.net/excellent-products-from-bioron/dna-rna-purification/one-tube-dna-purification.html>, 2 pages.

U.S. Appl. No. 29/321,200, filed Jul. 11, 2008, Wilson et al.

Bollet, C. et al., "A simple method for the isolation of chromosomal DNA from Gram positive or acid-fast bacteria", Nucleic Acids Research, vol. 19, No. 8 (1991), p. 1955.

Brahmassandra, et al., On-Chip DNA Detection in Microfabricated Separation Systems, Part of the SPIE Conference on Microfludic Devices and Systems, 1998, Santa Clara, California, vol. 3515, pp. 242-251.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

(56) References Cited

OTHER PUBLICATIONS

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Plambeck et al., "Electrochemical Studies of Antitumor Antibiotics", J. Electrochem Soc.: Electrochemical Science and Technology (1984), 131(11): 2556-2563.

Wang, "Survey and Summary, from DNA Biosensors to Gene Chips", Nucleic Acids Research, 28(16):3011-3016, (2000).

\* cited by examiner

REAGENT HOLDER, AND KITS CONTAINING SAME

CLAIM OF PRIORITY

This application claims the benefit of priority of U.S. provisional patent application Ser. No. 60/959,437, filed Jul. 13, 2007 which is incorporated herein by reference in its entirety.

TECHNICAL FIELD

The technology described herein generally relates to holders for reagents, such as may be used for transporting the reagents and for carrying out processing operations with the reagents. The technology more particularly relates to holders that hold reagents for preparing biological samples for amplifying and detecting polynucleotides extracted from the samples.

BACKGROUND

The medical diagnostics industry is a critical element of today's healthcare infrastructure. At present, however, diagnostic analyses no matter how routine have become a bottleneck in patient care. There are several reasons for this. For example, many diagnostic analyses can only be done with highly specialist equipment that is both expensive and only operable by trained clinicians. Such equipment is found in only a few locations, and often there is just one in any given urban area. This means that most hospitals are required to send out samples for analyses to these locations, thereby incurring shipping costs and transportation delays, and possibly even sample loss or mishandling.

Understanding that sample flow breaks down into several key steps, it would be desirable to consider ways to automate or make efficient as many of these as possible. In one key step, a biological sample, once extracted from a patient, must be put in a form suitable for a processing and detection regime that typically involves using PCR to amplify a vector of interest. Once amplified, the presence or absence of the vector in the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Furthermore, the reagents required are of sufficient variety that they typically require different handling from one another and are available from different vendors.

There is therefore a need for a method and apparatus of carrying out sample preparation on samples, such as in parallel, with or without PCR and detection on the prepared biological samples, and so that logistical inconveniences of reagent handling are reduced.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

A reagent holder comprising: a connecting member having an upper side and, opposed to the upper side, an underside; a process tube affixed to the connecting member and having an aperture located in the connecting member; at least one socket, located in the connecting member, the socket configured to accept a pipette tip; two or more reagent tubes disposed on the underside of the connecting member, each of the reagent tubes having an inlet aperture located in the connecting member; and one or more receptacles, located in the connecting member, wherein the one or more receptacles are each configured to receive a reagent tube inserted from the upper side of the connecting member.

A kit comprising: a first pouch containing one or more of the holders described herein; and a second pouch, having an inert atmosphere inside, and one or more tubes containing lyophilized PCR reagents.

A unitized reagent holder, comprising: a strip, to which is attached: a single process tube; one or more containers, each of which holding a reagent selected from the group consisting of: a sample preparation reagent, PCR reagents for a first analyte, and one or more liquid reagents; and one or more sockets configured to hold one or more pipette tips.

A reagent holder comprising: a process tube; one or more pipette tips; and one or more reagent tubes, wherein the one or more reagent tubes contain, respectively, sufficient quantities of one or more reagents for carrying out extraction of polynucleotides from a sample, and wherein the process tube, the one or more pipette tips, and the one or more reagent tubes are each joined to a single connecting member.

A reagent tube, comprising: a stellated pattern of cutouts or ridges centered at the bottom of the interior surface of the tube.

BRIEF DESCRIPTION OF THE DRAWINGS

Like reference numerals in the various drawings indicate like elements.

DETAILED DESCRIPTION

Described herein are reagent holders for holding and transporting reagents for various purposes, in particular sample preparation in a clinical context. The holder permits snapping in of one or more tubes of analyte specific reagents (ASR's) and/or sample preparation reagents, and carrying out liquid dispensing processes, associated with sample preparation, that minimize cross-sample contamination but permit multiple PCR preparations to be performed from a single clinical sample. The holders are configured for use in an automated preparatory apparatus that can carry out sample preparation on samples in more than one holder simultaneously.

The reagent holders as described herein find particular application to analyzing any nucleic acid containing sample for any purpose, including but not limited to genetic testing, and clinical testing for various infectious diseases in humans.

In various embodiments, preparation of a PCR-ready sample for use in subsequent diagnosis, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid). In some embodiments, the PCR reagent mixture can be in the form of one or more lyophilized pellets, as stored in a container on the holder, and the method can further include reconstituting the PCR pellet with liquid to create a PCR reagent mixture solution. The holder herein provides in a self-contained manner, all of the reagents required to prepare a PCR-ready sample, or, when delivered to a user in kit form, contains in conjunction with other packages all of the required reagents. Suitable reagents, and protocols for using the same in DNA and RNA extractions can be found in, respectively, copending application Ser. Nos. 12/172,208, and 12/172,214, both filed Jul. 11, 2008 and incorporated herein by reference.

The holders herein are also configured for use by an apparatus that carries out automated sample preparation, for example, on multiple samples simultaneously. An exemplary form of such an apparatus is further described herein, and can also be found described in U.S. provisional patent application Ser. No. 60/959,437, filed Jul. 13, 2007, incorporated herein by reference in its entirety.

Holder

Figure 1A:
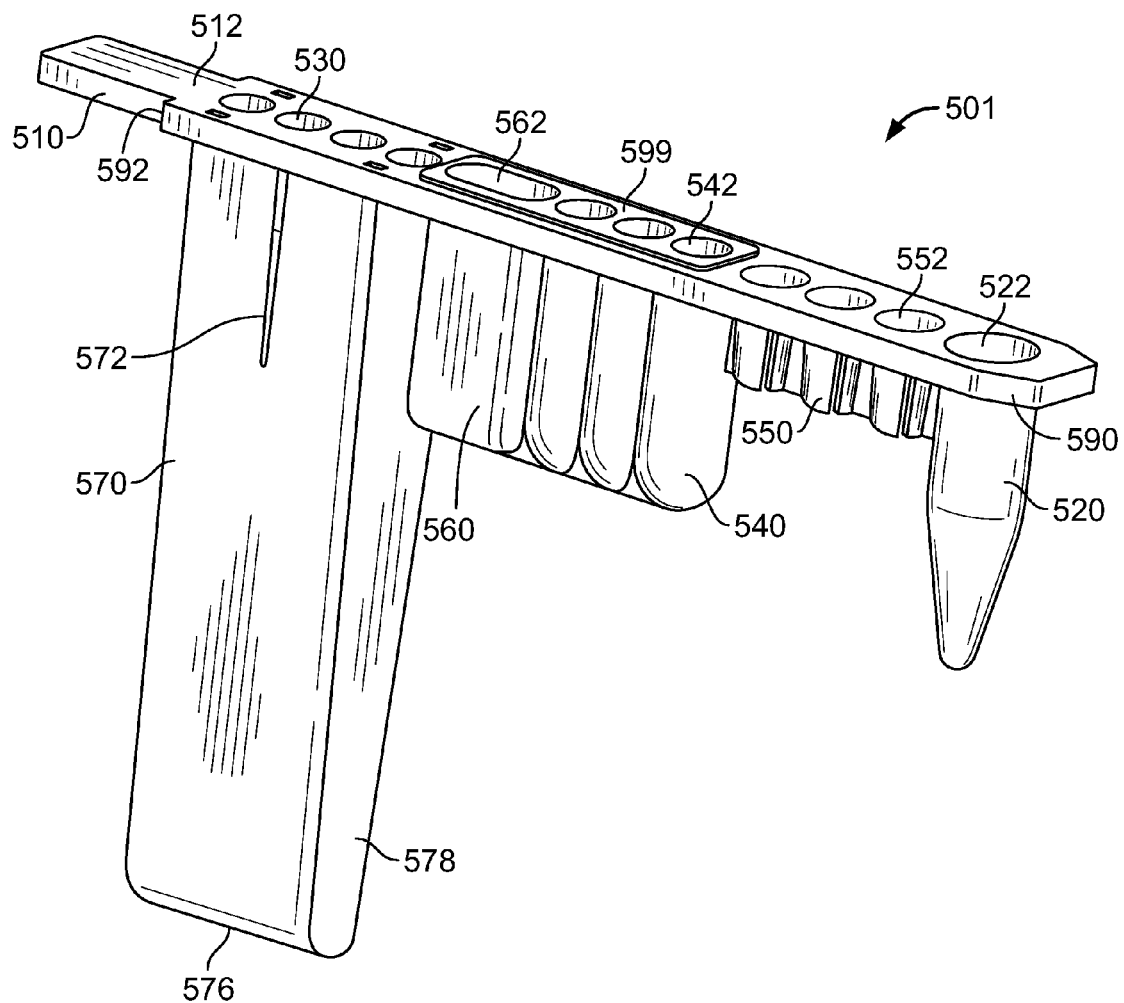
FIGS. 1A and 1B show an first exemplary embodiment of a reagent holder having a pipette sheath, in perspective view (FIG. 1A) and underside view (FIG. 1B).
Figure 1B:
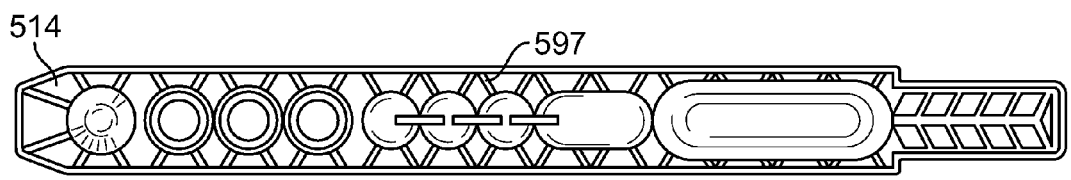
Figure 2:
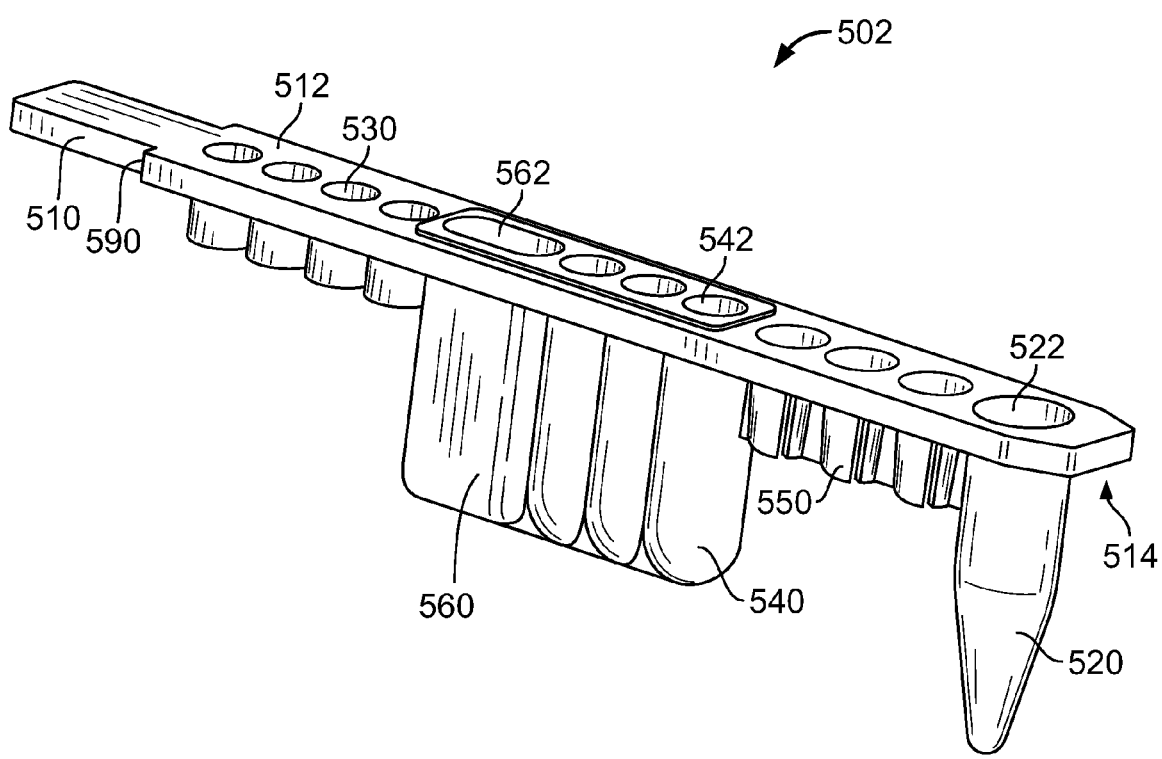
FIG. 2 shows an exemplary embodiment of a reagent holder not having a pipette sheath, in perspective view.
Figures 3A, 3B:
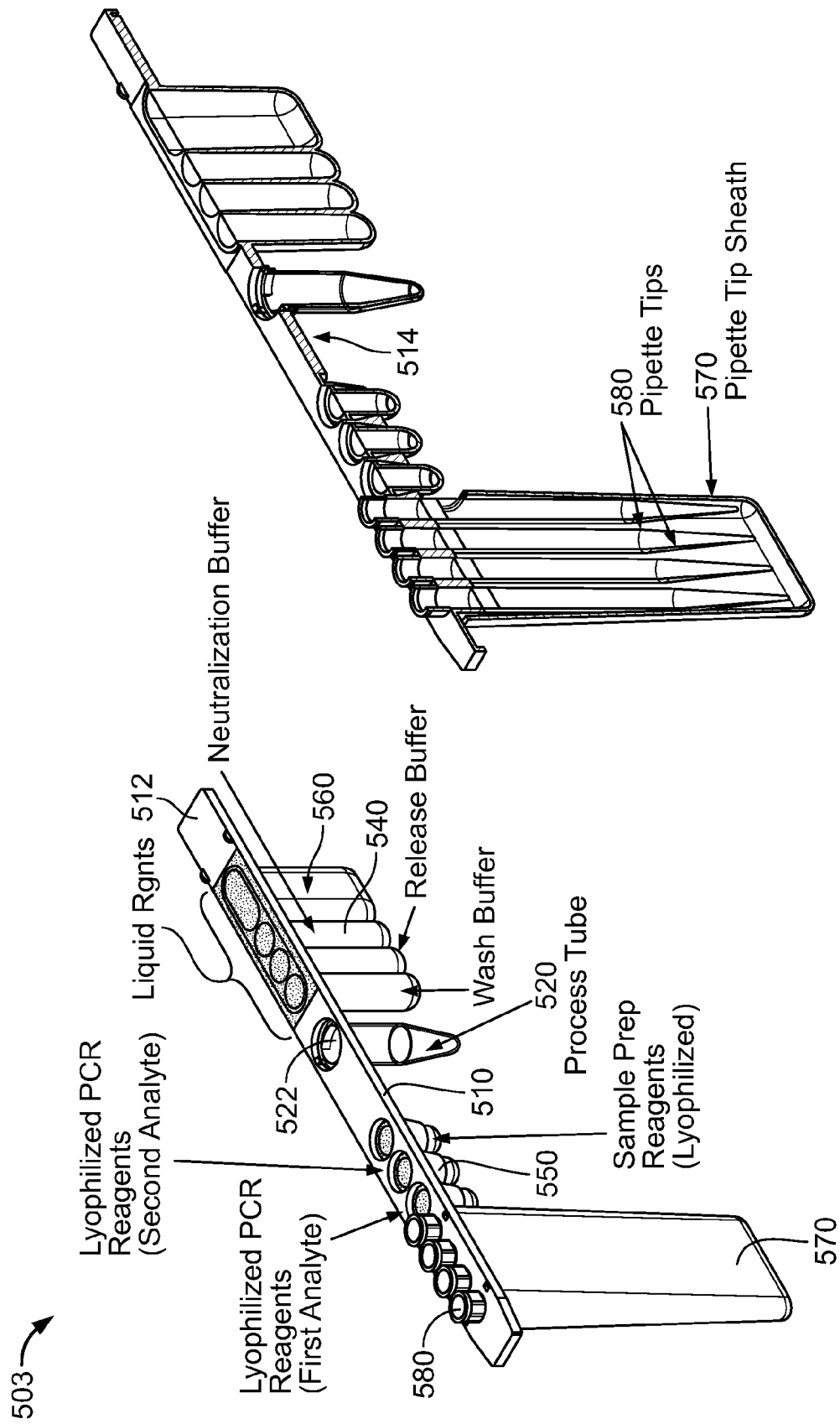
FIGS. 3A-3C show a second exemplary embodiment of a reagent holder having a pipette sheath, in perspective view (FIG. 3A) and cross-sectional view (FIG. 3B), and exploded view (FIG. 3C).
Figure 3C:
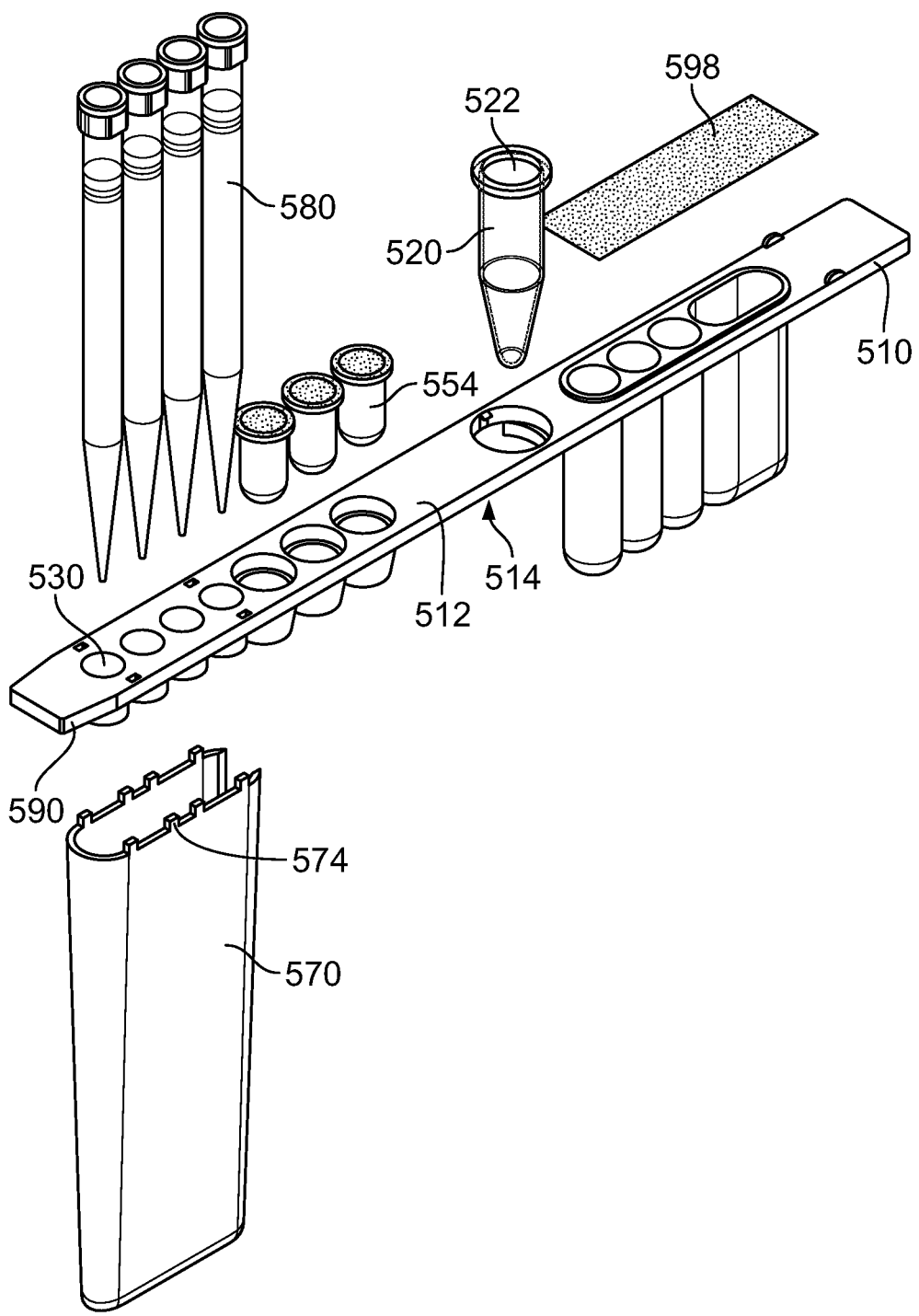

FIGS. 1A and 1B show views of an exemplary holder 501 as further described herein. FIG. 2 shows a plan view of another exemplary holder 502, as further described herein. FIG. 3A shows an exemplary holder 503 in perspective view, and FIG. 3B shows the same holder in cross-sectional view. FIG. 3C shows an exploded view of the same holder as in FIGS. 3A and 3B. All of these exemplary holders, as well as others consistent with the written description herein though not shown as specific embodiments, are now described.

The exemplary holders shown in FIGS. 1A, 1B, 2, 3A, 3B, and 3C can each be referred to as a "unitized disposable strip", or a "unitized strip", because they are intended to be used as a single unit that is configured to hold all of the reagents and receptacles necessary to perform a sample preparation, and because they are laid out in a strip format. It is consistent with the description herein, though, that other geometric arrangements of the various receptacles are contemplated, so that the description is not limited to a linear, or strip, arrangement, but can include a circular or grid arrangement.

Some of the reagents contained in the holder are provided as liquids, and others may be provided as solids. In some embodiments, a different type of container or tube is used to store liquids from those that store the solids.

The holder can be disposable, such as intended for a single use, following which it is discarded.

The holder is typically made of a plastic such as polypropylene. The plastic is such that it has some flexibility to facilitate placement into a rack, as further described herein. The plastic is typically rigid, however, so that the holder will not significantly sag or flex under its own weight and will not easily deform during routine handling and transport, and thus will not permit reagents to leak out from it.

The holder comprises a connecting member 510 having one or more characteristics as follows. Connecting member 510 serves to connect various components of the holder together. Connecting member 510 has an upper side 512 and, opposed to the upper side, an underside 514. In FIG. 1B, a view of underside 514 is shown, having various struts 597 connecting a rim of the connecting member with variously the sockets, process tube, and reagent tubes. Struts 597 are optional, and may be omitted all or in part, or may be substituted by, in all or in part, other pieces that keep the holder together.

The holder is configured to comprise: a process tube 520 affixed to the connecting member and having an aperture 522 located in the connecting member; at least one socket 530, located in the connecting member, the socket configured to accept a disposable pipette tip 580; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown) inserted from the upper side 512 of the connecting member.

The holder is typically such that the connecting member, process tube, and the two or more reagent tubes are made from a single piece, such as a piece of polypropylene.

The holder is also typically such that at least the process tube, and the two or more reagent tubes are translucent.

The one or more receptacles 550 are configured to accept reagent tubes that contain, respectively, sufficient quantities of one or more reagents typically in solid form, such as in lyophilized form, for carrying out extraction of nucleic acid from a sample that is associated with the holder. The receptacles can be all of the same size and shape, or may be of different sizes and shapes from one another. Receptacles 550 are shown as having open bottoms, but are not limited to such topologies, and may be closed other than the inlet 552 in the upper side of connecting member 510. Preferably the receptacles 550 are configured to accept commonly used containers in the field of laboratory analysis, or containers suitably configured for use with the holder herein. The containers are typically stored separately from the holders to facilitate sample handling, since solid reagents normally require different storage conditions from liquid reagents. In particular many solid reagents may be extremely moisture sensitive.

The snapped-in reagent tubes containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a barcode on the sealing layer on the top.

The containers 554 received by the receptacles 550 may alternatively be an integrated part of the holder and may be the same type of container as the waste chamber and/or the reagent tube(s), or may be different therefrom.

Figure 4B:
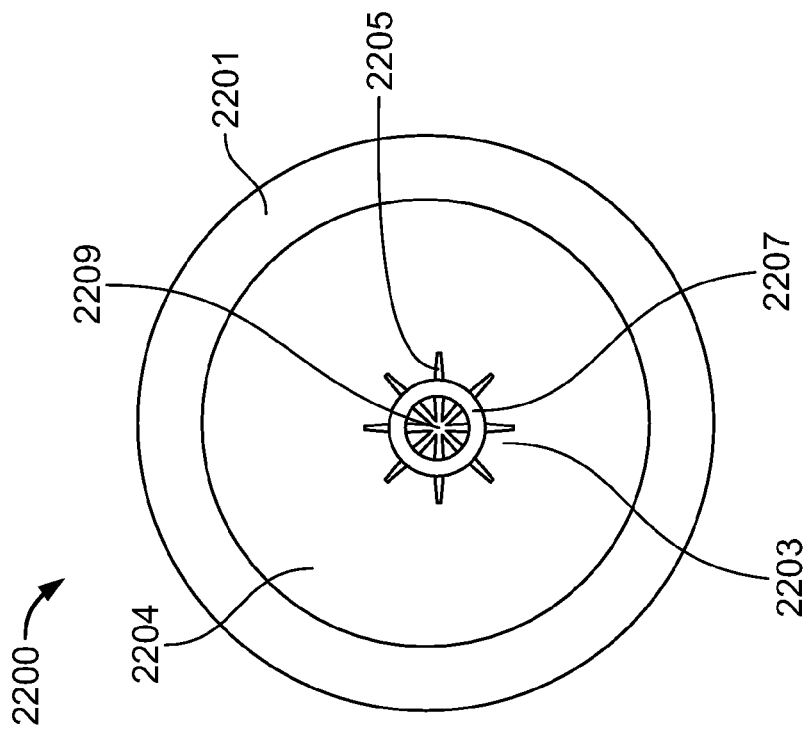
FIGS. 4A and 4B show a stellated feature on the interior of a reagent tube, in cross-sectional (FIG. 4A) and plan (FIG. 4B) view.

In one embodiment, the containers 554 containing lyophilized reagents, disposed in the receptacles 550 (shown, e.g., in FIGS. 3A and 3C), are 0.3 ml tubes that have been further configured to have a star pattern (see FIGS. 4A and 4B) on their respective bottom interior surfaces. This is so that when a fluid has been added to the lyophilized reagents (which are dry in the initial package), a pipette tip can be bottomed out in the tube and still be able to withdraw almost the entire fluid from the tube, as shown in FIG. 5, during the process of nucleic acid extraction. The design of the star-pattern is further described elsewhere herein.

The reagent tubes, such as containing the lyophilized reagents, can be sealed across their tops by a metal foil, such as an aluminum foil, with no plastic lining layer, as further described herein.

The embodiments 501, 502, and 503 are shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed. Waste chamber 560 is shown as part of an assembly comprising additionally two or more reagent tubes 540. It would be understood that such an arrangement is done for convenience, e.g., of manufacture; other locations of the waste chamber are possible, as are embodiments in which the waste chamber is adjacent a reagent tube, but not connected to it other than via the connecting member.

The holder is typically such that the connecting member, process tube, the two or more reagent tubes, and the waste chamber (if present) are made from a single piece, made from a material such as polypropylene.

The embodiments 501 and 503 are shown having a pipette sheath 570. This is an optional component of the holders described herein. It may be permanently or removably affixed to connecting member 510, or may be formed, e.g., moulded, as a part of a single piece assembly for the holder. For example, exploded view of holder 503 in FIG. 3C shows lug-like attachments 574 on the upper surface of a removable pipette sheath 570 that engage with complementary recessed portions or holes in the underside 514 of connecting member 510. Other configurations of attachment are possible. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. Such cutouts provide ventilation for the pipette tips and also reduce the total amount of material used in manufacture of the holder. Embodiment 503 has a pipette sheath with no such cutouts. In embodiment 501, such a cutout is shown as an isosceles triangle in the upper portion of the sheath; a similar shaped cutout may be found at a corresponding position in the opposite side of the sheath, obscured from view in FIG. 1A. Other cutouts could have other triangular forms, circular, oval, square, rectangular, or other polygonal or irregular shapes, and be several, such as many, in number. The wall 578 of pipette sheath 570 may also have a mesh or frame like structure having fenestrations or interstices. In embodiments having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment such as 502, having no pipette sheath, could utilize, e.g., a drip tray or a drainage outlet, suitably placed beneath pipette tips located in the one or more sockets, for the same purpose. In addition to catching drips, the pipette tip sheath prevents or inhibits the tips of other reagent holders—such as those that are situated adjacent to the one in question in a rack as further described herein—from touching each other when the tips are picked up and/or dropped off before or after some liquid processing step. Contact between tips in adjacent holders is generally not intended by, for example, an automated dispensing head that controls sample processing on holders in parallel, but the pipette tips being long can easily touch a tip in a nearby strip if the angle when dropping off of the tip deviates slightly from vertical.

The holders of embodiments 501, 502, and 503, all have a connecting member that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, waste chamber, process tube, sockets, and reagent tubes. For example, a holder may be made shorter, if some apertures are staggered with respect to one another and occupy 'off-axis' positions. The various receptacles, etc., also do not need to occupy the same positions with respect to one another as is shown in FIGS. 3A and 3B, wherein the process tube is disposed approximately near the middle of the holder, liquid reagents are stored in receptacles mounted on one side of the process tube, and receptacles holding solid reagents are mounted on the other side of the process tube. Thus, in FIGS. 1A, 1B, and 2, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein.

Process tube 520 can also be a snap-in tube, rather than being part of an integrated piece. Process tube 520 is typically used for various mixing and reacting processes that occur during sample preparation. For example, cell lysis can occur in process tube 520, as can extraction of nucleic acids. Process tube 520 is then advantageously positioned in a location that minimizes, overall, pipette head moving operations involved with transferring liquids to process tube 520.

Reagent tubes 540 are typically configured to hold liquid reagents, one per tube. For example, in embodiments 501, 502, and 503, three reagent tubes are shown, containing respectively wash buffer, release buffer, and neutralization buffer, each of which is used in a sample preparation protocol.

Reagent tubes 540 that hold liquids or liquid reagents can be sealed with a laminate structure 598. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum.

Figure 6:
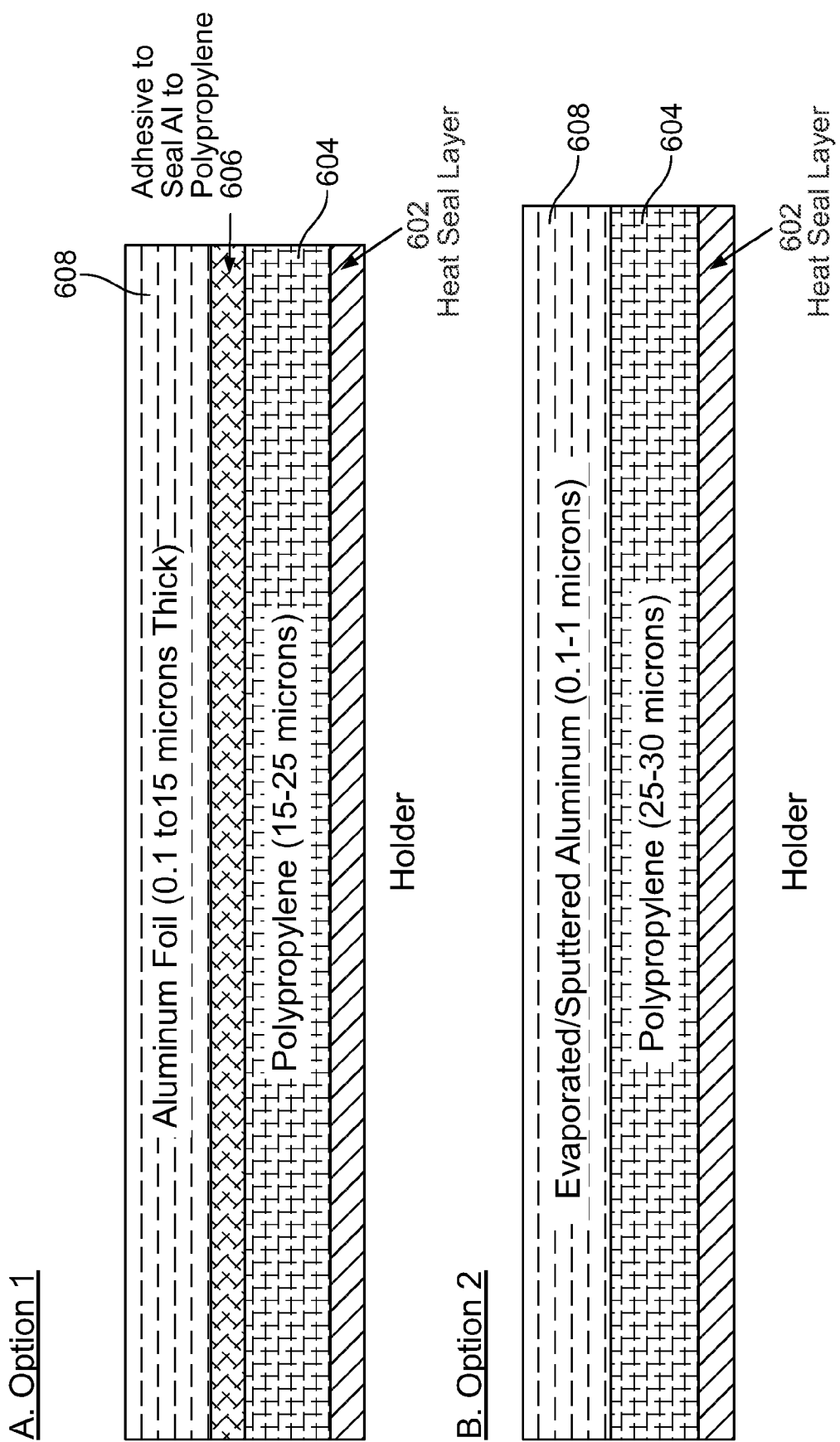
FIG. 6 shows embodiments of a laminated layer.

Two embodiments of a laminate structure, differing in their layer structures, are shown in FIG. 6. In both embodiments, the heat seal layer 602, for example made of a laquer or other such polymer with a low melting point, is at the bottom, adjacent to the top of the holder, when so applied. The plastic layer 604 is typically on top of the heat seal layer, and is typically made of polypropylene, having a thickness in the range 10-50 microns. The metal layer 608 is typically on top of the plastic layer and may be a layer of Al foil bonded to the plastic layer with a layer of adhesive 606, as in the first embodiment in FIG. 6, or may be a layer of metal that is evaporated or sputtered into place directly on to the plastic layer. Exemplary thicknesses for the respective layers are shown in FIG. 6, where it is to be understood that variations of up to a factor of 2 in thickness are consistent with the technology herein. In particular, the aluminum foil is 0.1-15 microns thick, and the polymer layer is 15-25 microns thick in one embodiment. In another embodiment, the aluminum is 0.1-1 microns thick, and the polymer layer is 25-30 microns thick.

The laminates deployed herein make longer term storage easier because the holder includes the presence of sealed lyophilized reagents as well as liquids sealed in close proximity, which is normally hard to achieve.

In one embodiment, the tops of the reagent tubes have beveled edges so that when an aluminum foil is heat bonded to the top, the plastic melt does not extend beyond the rim of the tube. This is advantageous because, if the plastic melt reduces the inner diameter of the tube, it will cause interference with the pipette tip during operation. In other embodiments, a raised flat portion 599 facilitates application and removal of laminate 598. Raised surface 599, on the upper side of the connecting member, and surrounding the inlet apertures to the reagent tubes and, optionally, the waste chamber, is an optional feature of the holder.

Figure 7:
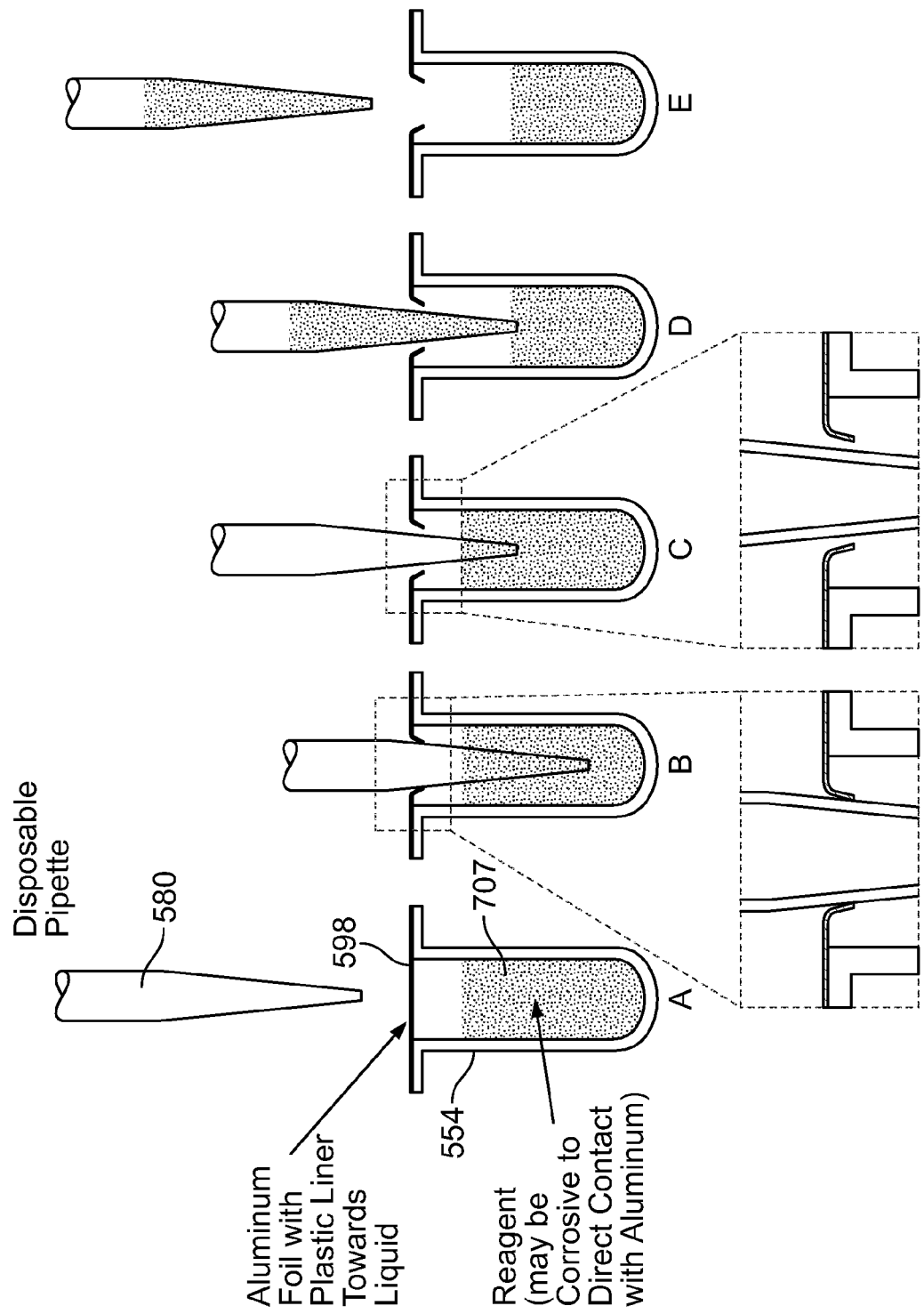
FIG. 7 shows a sequence of pipetting operations in conjunction with a laminated layer.
Figure 8A:
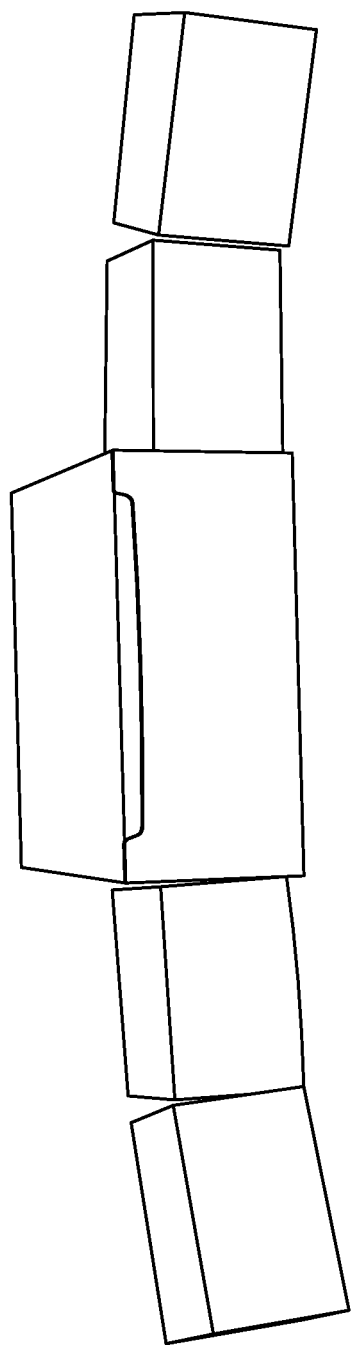
FIGS. 8A-8D shows an exemplary kit containing holders and reagents.
Figure 8B:
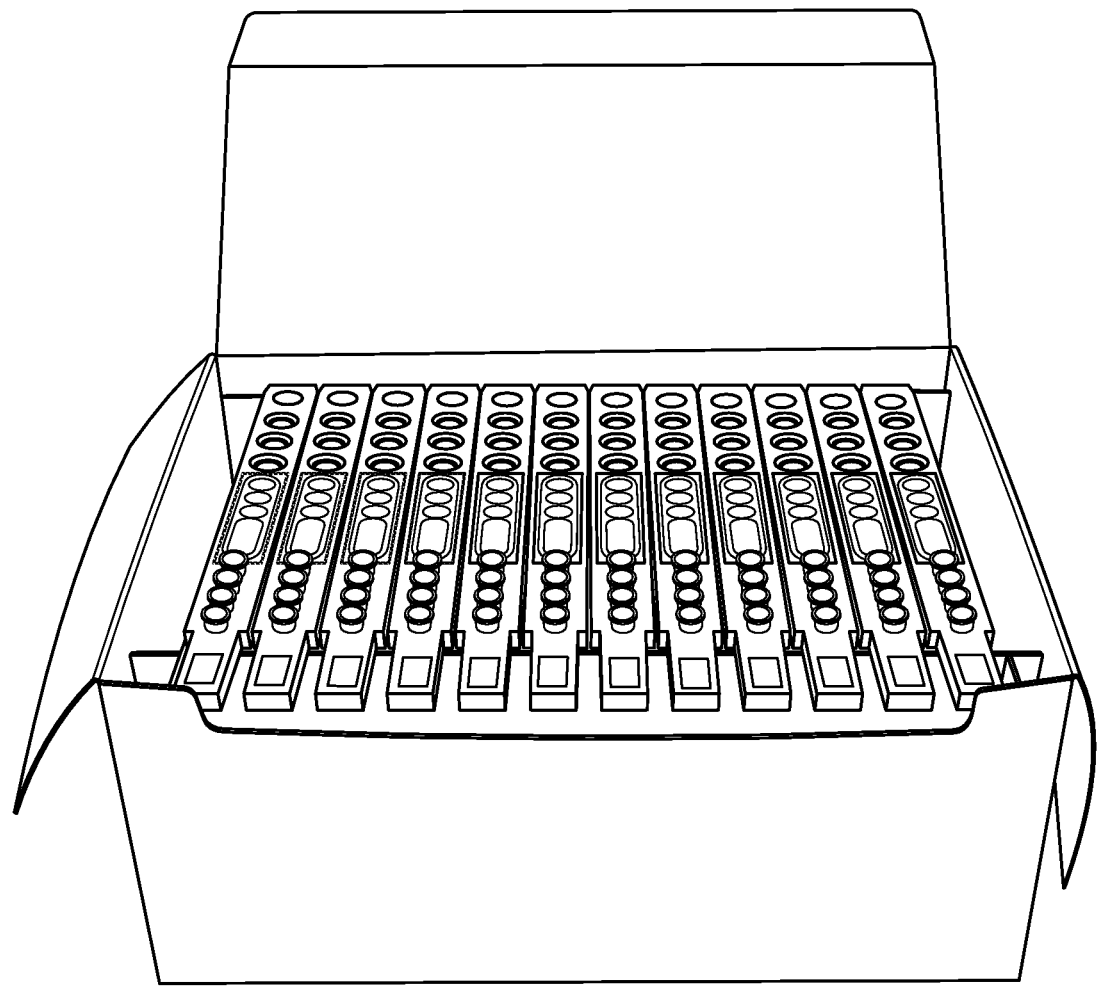
Figure 8C:
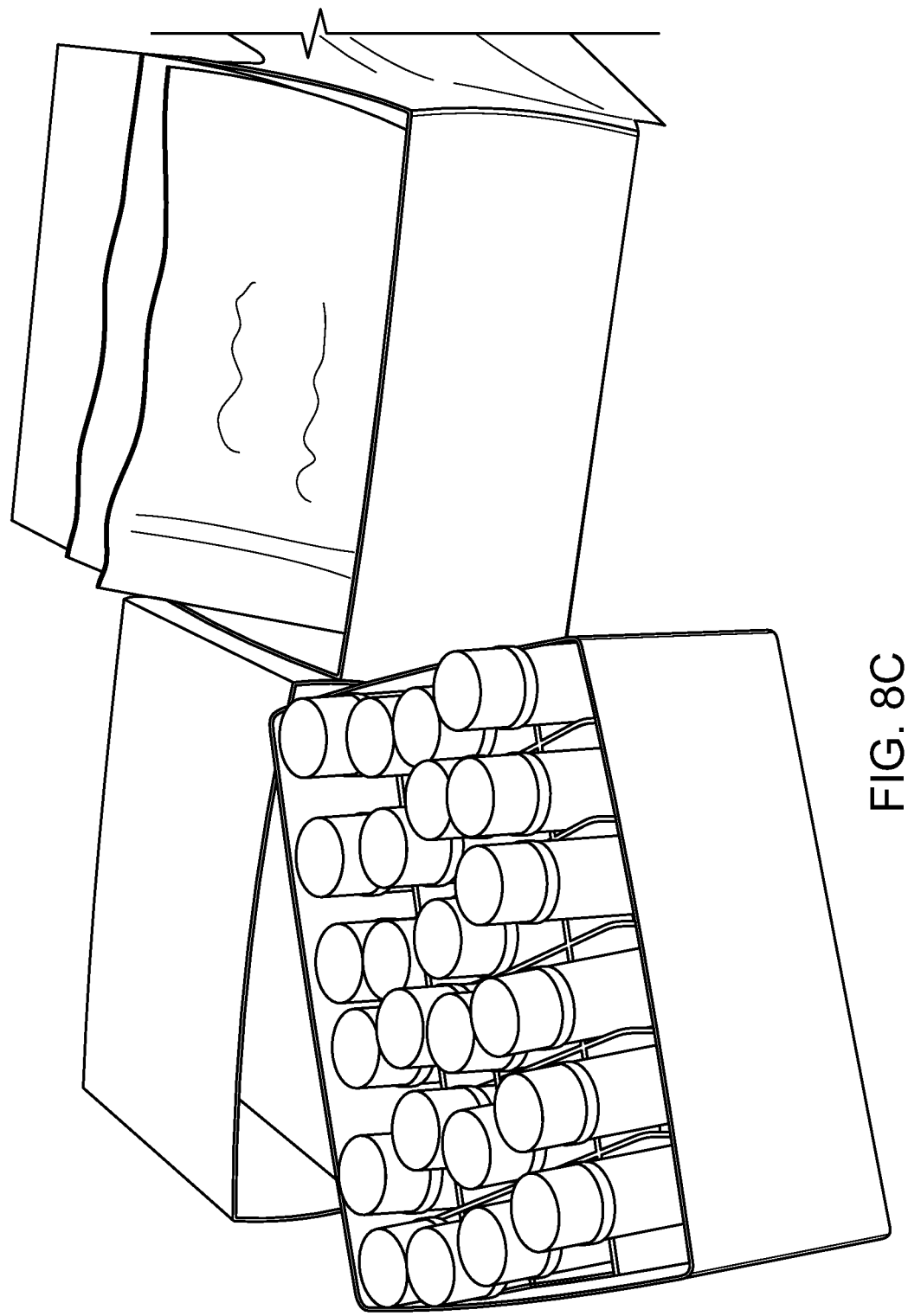
Figure 8D:
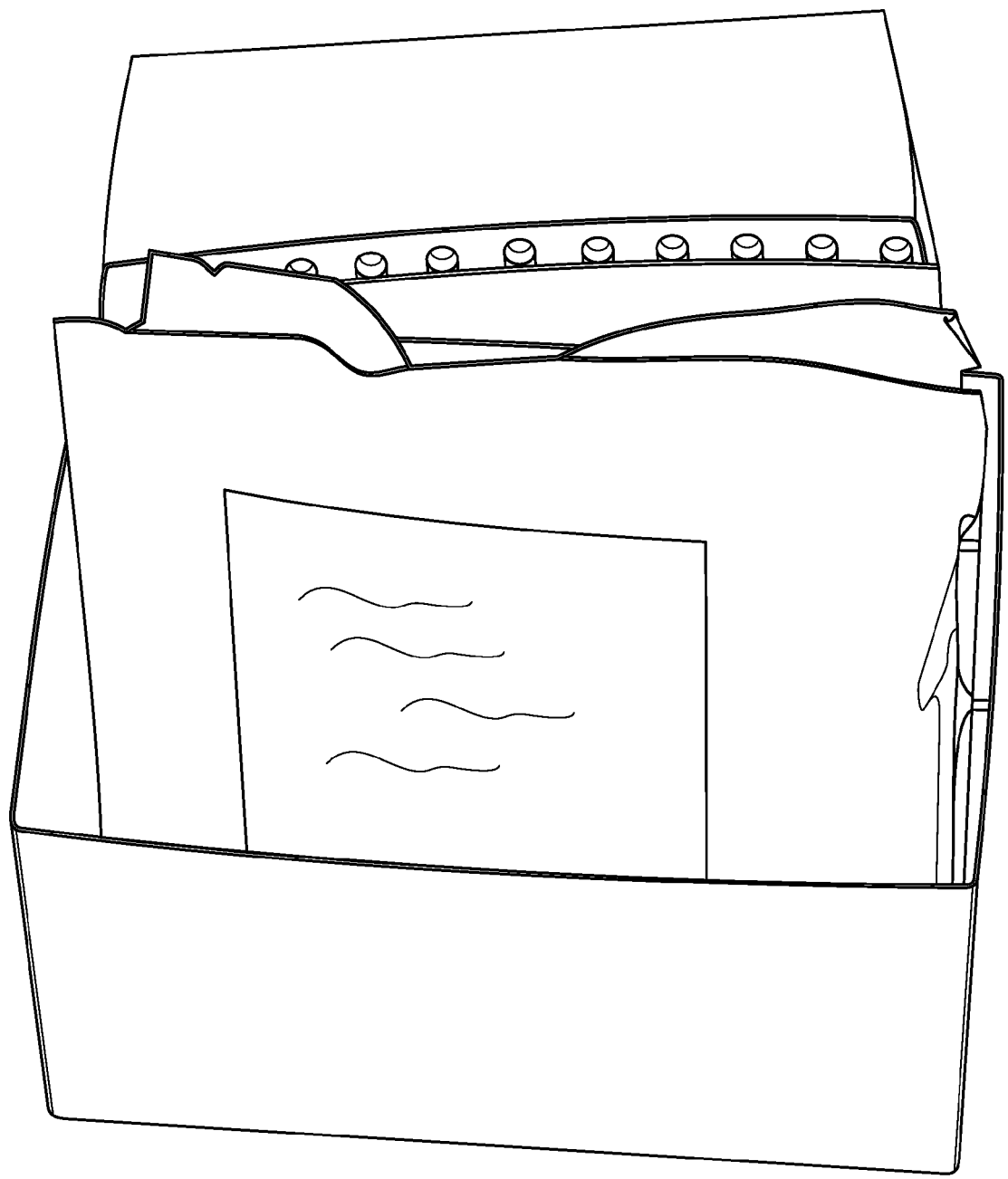

The manner in which liquid is pipetted out is such that a pipette tip piercing through the foil rips through without creating a seal around the pipette tip, as in FIG. 7. Such a seal around the tip during pipetting would be disadvantageous because a certain amount of air flow is desirable for the pipetting operation. In this instance, a seal is not created because the laminate structure causes the pierced foil to stay in the position initially adopted when it is pierced. The upper five panels in FIG. 7 illustrate the pipetting of a reagent out from a reagent tube sealed with a laminate as further described herein. At A, the pipette tip is positioned approximately centrally above the reagent tube that contains reagent 707. At B, the pipette tip is lowered, usually controllably lowered, into the reagent tube, and in so doing pierces the foil 598. The exploded view of this area shows the edge of the pierced laminate to be in contact with the pipette tip at the widest portion at which it penetrates the reagent tube. At C, the pipette tip is withdrawn slightly, maintaining the tip within the bulk of the reagent 707. The exploded view shows that the pierced foil has retained the configuration that it adopted when it was pierced and the pipette tip descended to its deepest position within the reagent tube. At D, the pipette tip sucks up reagent 707, possibly altering its height as more and more older people undergo such tests. At E, the pipette tip is removed entirely from the reagent tube.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

In some embodiments, the holder comprises a registration member such as a mechanical key. Typically such a key is part of the connecting member 510. A mechanical key ensures that the holder is accepted by a complementary member in, for example, a supporting rack or a receiving bay of an apparatus that controls pipetting operations on reagents in the holder. A mechanical key is normally a particular-shaped cut-out that matches a corresponding cutout or protrusion in a receiving apparatus. Thus, embodiment 501 has a mechanical key 592 that comprises a pair of rectangular-shaped cut-outs on one end of the connecting member. This feature as shown additionally provides for a tab by which a user may gain a suitable purchase when inserting and removing the holder into a rack or another apparatus. Embodiments 501 and 502 also have a mechanical key 590 at the other end of connecting member 510. Key 590 is an angled cutout that eases insertion of the holder into a rack, as well as ensures a good registration therein when abutting a complementary angled cut out in a recessed area configured to receive the holder. Other variations of a mechanical key are, of course, consistent with the description herein: for example, curved cutouts, or various combinations of notches or protrusions all would facilitate secure registration of the holder.

In some embodiments, not shown in FIG. 1A, 1B, 2, or 3A-C, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample is accessible to a sample identification verifier.

Kits

The holder described herein may be provided in a sealed pouch, to reduce the chance of air and moisture coming into contact with the reagents in the holder. Such a sealed pouch may contain one or more of the holders described herein, such as 2, 4, 6, 8, 10, 12, 16, 20, or 24 holders.

The holder may also be provided as part of a kit for carrying out sample preparation, wherein the kit comprises a first pouch containing one or more of the holders described herein, each of the holders configured with liquid reagents for, e.g., lysis, wash, and release, and a second pouch, having an inert atmosphere inside, and one or more reagent tubes containing lyophilized PCR reagents, as shown in FIGS. 8A-D. Such a kit may also be configured to provide for analysis of multiple samples, and contain sufficient PCR reagents (or other amplification reagents, such as for RT-PCR, transcription mediated amplification, strand displacement amplification, NASBA, helicase dependent amplification, and other familiar to one of ordinary skill in the art, and others described herein) to process such samples, and a number of individual holders such as 2, 4, 6, 8, 10, 12, 16, 20, or 24 holders.

Reagent Tubes

As referenced elsewhere herein, the containers 554 that contain lyophilized reagents are 0.3 ml tubes that have been further configured to have a star-shaped—or stellated—pattern (see FIGS. 4A and 4B) on their respective bottom interior surfaces. Still other tubes for use herein, as well as for other uses not herein described, can be similarly configured. Thus, for example, the benefits afforded by the star-shaped pattern also accrue to reagent tubes that contain liquid samples that are directly pipetted out of the tubes (as well as to those tubes that initially hold solids that are constituted into liquid form prior to pipetting). Other size tubes that would benefit from such a star-shaped pattern have sizes in the range 0.1 ml to 0.65 ml. for example.

The star-shaped pattern ensures that when a fluid is withdrawn from the tube, a pipette tip can be bottomed out in the tube and still be able to withdraw the entire, or almost the entire fluid from the tube, as shown in FIG. 5. This is important because, when working with such small volumes, and when target DNA can be present in very few copies, sample loss due to imperfections of pipetting is to be minimized to every extent possible.

The design of the star shaped pattern is important, especially when using for recovery of DNA/RNA present in very small numbers in the clinical sample. The stellated pattern should enable pipetting of most of the liquid (residual volume <1 microliter) when used with a pipette bottomed out with the bottom of the tube. Additionally, the stellated pattern should be designed to minimize surface area as well as dead-end grooves that tend to have two undesirable effects—to trap liquid as well as to increase undesirable retention of polynucleotides by adsorption.

FIG. 5 is now described, as follows. FIG. 5 has a number of panels, A-G, each representing, in sequence, a stage in a pipetting operation. At A, a pipette tip 2210, containing a liquid 2211 (such as a buffer solution), is positioned directly or approximately above the center of reagent tube 2200. The tube contains a number of lyophilized pellets 2212, and is sealed by a layer 2214, such as of foil. The foil may be heat-sealed on to the top of the tube. Although a laminate layer, as further described herein, can be placed on the reagent tube, typically a layer of aluminum foil is adequate, where the tube contents are solid, e.g., lyophilized, reagents. In some embodiments, the top of the reagent tube has chamfer edges to reduce expansion of the top rim of the tube during heat sealing of a foil on the top of the tube. The tube may further comprise an identifiable code, such as a 1-D or a 2-D bar-code on the top. Such a code is useful for identifying the composition of the reagents stored within, and/or a batch number for the preparation thereof, and/or an expiry date. The code may be printed on with, for example, an inkjet or transfer printer.

Stellated pattern 2203 on the bottom interior surface of the tube 2200 is shown. At B, the pipette tip is lowered, piercing seal 2214, and brought into a position above the particles 2212. At C the liquid 2211 is discharged from the pipette tip on to the particles, dissolving the same, as shown at D. After the particles are fully dissolved, forming a solution 2218, the pipette tip is lowered to a position where it is in contact with the stellated pattern 2203. A E, the pipette tip is caused to suck up the solution 2218, and at F, the tip may optionally discharge the solution back into the tube. Steps E and F may be repeated, as desired, to facilitate dissolution and mixing of the lyophilized components into solution. At step G, after sucking up as much of the solution 2218 as is practicable into the pipette tip, the pipette tip is withdrawn from the tube. Ideally, 100% by volume of the solution 2218 is drawn up into the pipette tip at G. In other embodiments, and depending upon the nature of solution 2218, at least 99% by volume of the solution is drawn up. In still other embodiments, at least 98%, at least 97%, at least 96%, at least 95%, and at least 90% by volume of the solution is drawn up.

The design of the stellated or star-shaped pattern can be optimized to maximize the flow rate of liquid through the gaps in-between a bottomed out pipette, such as a p1000 pipette, and the star pattern, and is further described in U.S. provisional patent application Ser. No. 60/959,437, filed Jul. 13, 2007, incorporated herein by reference. It would be understood that, although the description herein pertains to pipettes and pipette tips typically used in sample preparation of biological samples, the principles and detailed aspects of the design are as applicable to other types of pipette and pipette tip, and may be so-adapted.

Figure 4A:
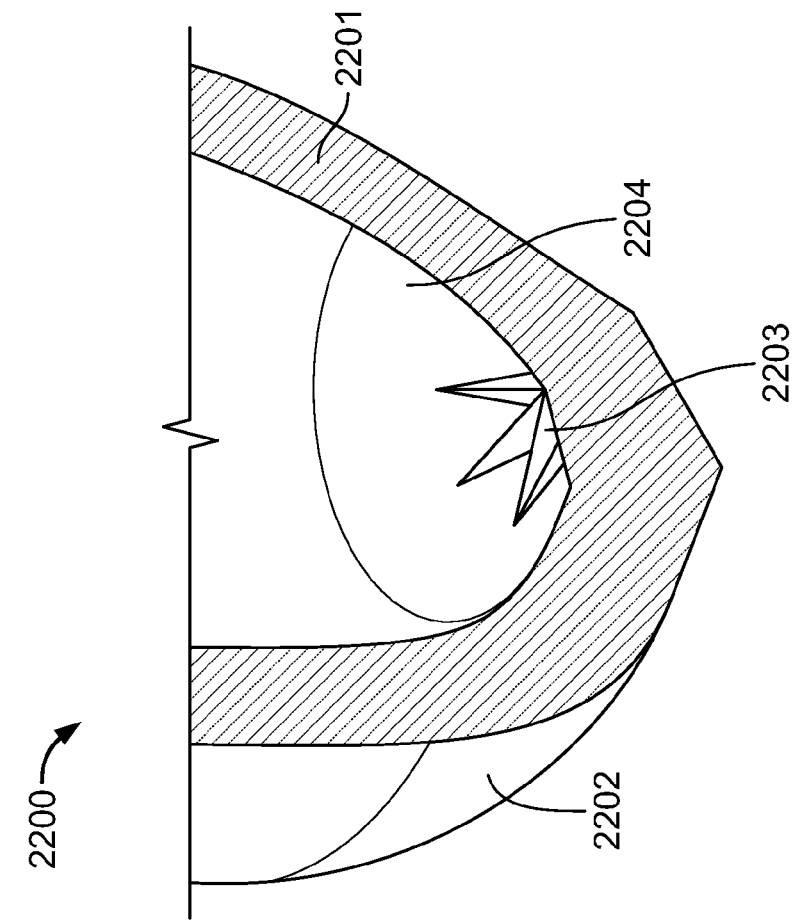
Figure 5:
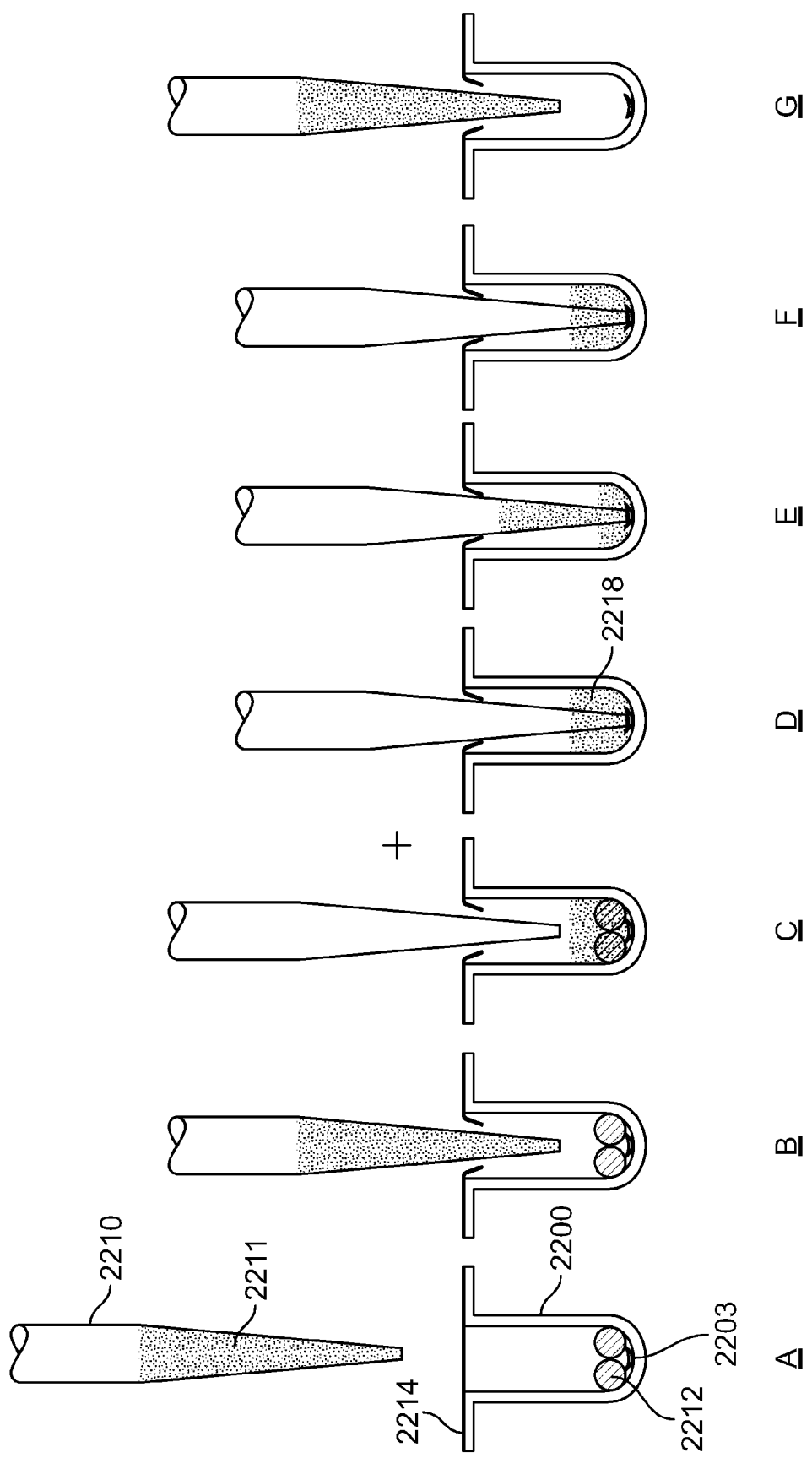
FIG. 5 shows a sequence of pipetting operations in conjunction with a reagent tube having a stellated feature.

FIG. 4A shows a cross sectional perspective view of a reagent tube 2200 having side wall 2201 and bottom 2202. Interior surface 2204 of the bottom is visible. A star-shaped cutout 2203 is shown in part, as three apical grooves.

Typically the star-shaped pattern is present as a raised portion on the lower interior surface of the tube. Thus, during manufacture of a reagent tube, such as by injection moulding, an outer portion of the mould is a cavity defining the exterior shape of the tube. An interior shape of the tube is formed by a mould positioned concentrically with the outer portion mould, and having a star-shaped structure milled out of its tip. Thus, when liquid plastic is injected into the space between the two portions of the mould, the star-shape is formed as a raised portion on the bottom interior surface of the tube.

The exemplary star pattern 2203 shown in FIG. 4B in plan view resembles a "ship's wheel" and comprises a center 2209, a circular ring 2207 centered on center 2209, and 8 radial segments configured as radial grooves 2205. Each groove meets the other grooves at center 2209, and has a radial end, also referred to as an apex or vertex. Star pattern 2203 has 8 grooves, but it would be understood that a star pattern having fewer or a greater number of grooves, such as 3, 4, 6, 10, or 12, would be consistent with the design herein. The number of grooves of the star should be minimum consistent with effective liquid pipetting and also spaced apart enough not to trap the tip of any of the pipette tips to be used in the liquid handling applications.

Center 2209 is typically positioned coincidentally with the geometric center of the bottom of reagent tube 2200. The tube is typically circular in cross-section, so identifying its center (e.g., at a crossing point of two diameters) is normally straightforward. Center 2209 may be larger than shown in FIG. 4B, such as may be a circular cutout or raised portion that exceeds in diameter of the region formed by the meeting point of grooves 2205.

Ring 2207 is an optional feature of star-shaped pattern 2203. Typically ring 2207 is centered about center 2209, and typically it also has a dimension that corresponds to the lower surface of a pipette tip. Thus, when a pipette tip 'bottoms out' in the bottom of reagent tube 2200, the bottom of the pipette tip rests in contact with ring 2207. Ring 2207 is thus preferably a cut-our or recessed feature that can accommodate the pipette tip and assist in guiding its positioning centrally at the bottom of the tube. In other embodiments more than one, such as 2, 3, or 4 concentric rings 2207 are present.

The star pattern is configured to have dimensions that give an optimal flow-rate of liquid out of the reagent tube into a suitably positioned pipette tip. The star pattern is shown in FIG. 4B as being significantly smaller in diameter than the diameter of the tube at its widest point. The star pattern may have, in various embodiments, a diameter (measured from center 2209 to apex of a groove 2205) from 5-20% of the diameter of the reagent tube, or from 10-25% of the diameter of the reagent tube, or from 15-30% of the diameter of the reagent tube, or from 20-40% of the diameter of the reagent tube, or from 25-50% of the diameter of the reagent tube, or from 30-50% the diameter of the reagent tube, or from 40-60% the diameter of the reagent tube, or from 50-75% the diameter of the reagent tube, or from 65-90% the diameter of the reagent tube.

The grooves 2205 are thus separated by ridges (occupying the space in between adjacent grooves). In the embodiment shown, the grooves are narrower (occupy a smaller radial angle) than the gaps between them. In other embodiments, the grooves may be proportionately wider than the gaps between them. In such embodiments, it may be more appropriate to describe them as having ridges instead of grooves. In other embodiments, the grooves and ridges that separate them are of equal widths at each radial distance from the center.

The grooves that form the apices of the star may be rounded in their lower surfaces, such as semi-circular in cross section, but are typically V-shaped. They may also be trapezoid in cross-section, such as having a wider upper portion than the bottom, which is flat, the upper portion and the bottom being connected by sloping walls.

In some embodiments, for ease of manufacture, the grooves end on the same level in the bottom of the tube. Thus the radial ends are all disposed on the circumference of a circle. In other embodiments, the grooves do not all end on the same level. For example, grooves may alternately end on different levels, and thus the ends are alternately disposed on the respective circumferences of two circles that occupy different planes in space from one another.

Grooves 2205 are shown in FIG. 4B as having equal lengths (as measured from center 2209 to apex). This need not be so. In alternative embodiments, grooves may have different lengths from one another, for example, as alternating lengths on alternating grooves, where there are an even number of grooves. Furthermore, apices may be rounded, rather than pointed.

Typically the grooves taper uniformly in width and depth from center 2209 to each respective apex. Still other configurations are possible, such as a groove that follows a constant width, or depth, out to a particular radial extent, such as 30-60% of its length, and then narrows or becomes shallower towards its apex. Alternatively, a groove may start narrow at center 2209, widen to a widest region near its midpoint of length, and then narrow towards its apex. Still other possibilities, not described herein, are consistent with the stellated pattern.

In a 0.3 ml tube, the width of each groove 2205 at its widest point is typically around 50 microns, and the width typically tapers uniformly from a widest point, closest to or at center 2209, to the apex.

In a 0.3 ml tube, the depth of a groove at the deepest point is typically around 25-50 microns and the depth typically tapers uniformly from a deepest point, closest to or at center 2209, to an apex.

In a 0.3 ml tube, the radius of the star formed from the grooves, measured as the shortest distance from center 2209 to apex, is typically around 0.5 mm, but may be from 0.1-1 mm, or from 0.3-2 mm.

In another embodiment, in a 0.3 ml tube, the grooves should be rounded off and less than 100 microns deep, or less than 50 microns deep, or less than 25 microns deep.

The stellated pattern typically has a rotation axis of symmetry, the axis disposed perpendicular to the bottom of the tube and through center 2209, so that the grooves are disposed symmetrically about the rotation axis. By this is meant that, for n grooves, a rotation of $2\pi/n$ about the central (rotational) axis can bring each groove into coincidence with the groove adjacent to it.

The stellated shape shown in FIG. 4B is not limiting in that it comprises a number of radially disposed grooves 2205, and an optional circular ring 2207. Other star-shaped geometries may be used, and, depending upon ease of manufacture, may be preferred. For example, a star can be created simply be superimposing two or more polygons having a common center, but offset rotationally with respect to one another about the central axis. (See, for example "star polygons" described at http://mathworld.wolfram.com/Star-Polygon.html.) Such alternative manners of creating star-shaped patterns are utilizable herein.

Rack

Figure 9:
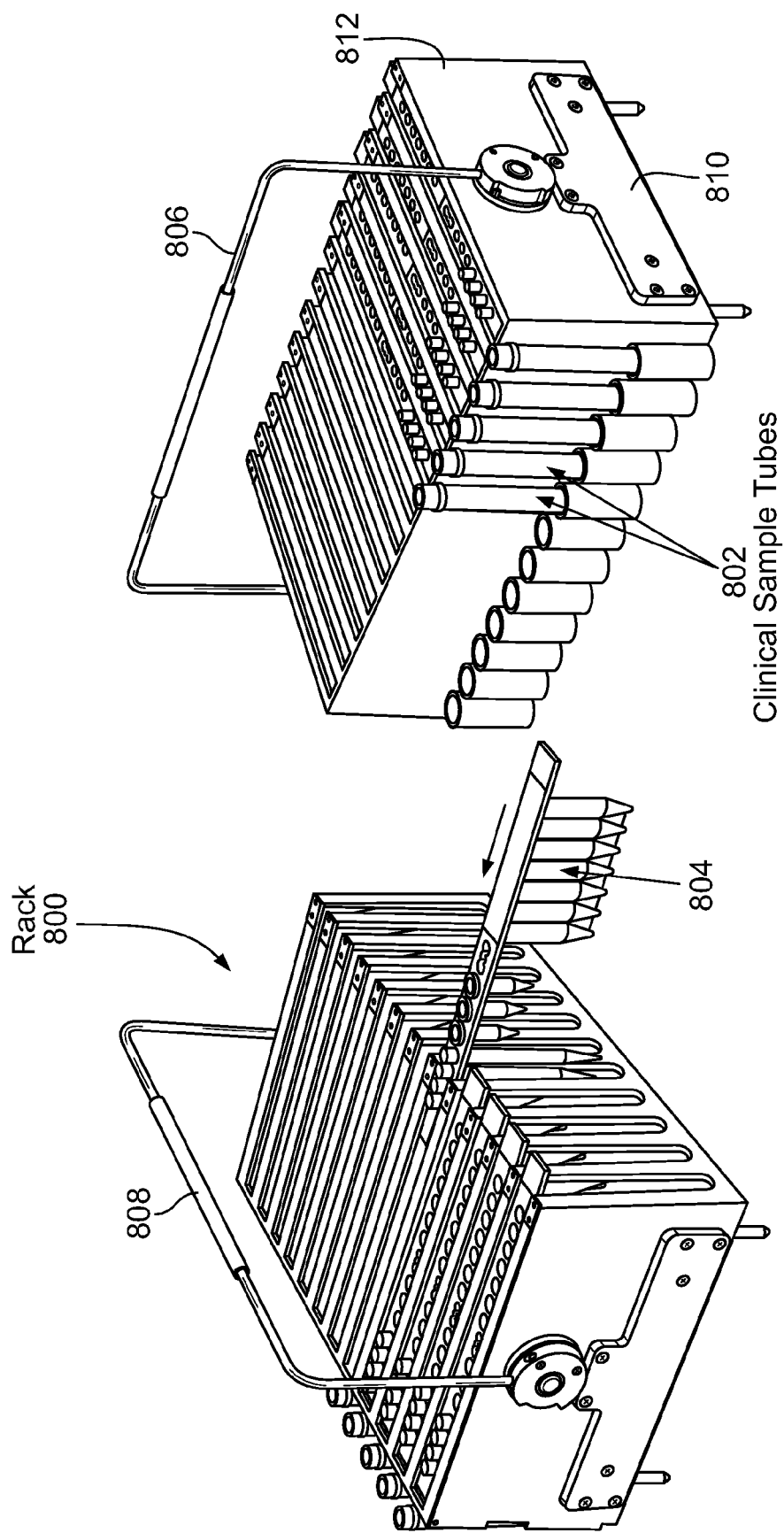
FIG. 9 shows a rack for holding one or more holders.

The holders herein are typically configured to fit into a dedicated rack, the rack being configured to hold one or more such holders, either on a laboratory benchtop, or situated in a dedicated apparatus having one or more other functions, such as automated pipetting. Two perspective views of an exemplary rack 800, configured to accept 12 sample tubes and 12 holders, are shown in FIG. 9.

For example, a rack may accept 2, 4, 6, 8, 10, 12, 16, or 20 samples, in sample tubes 802, and corresponding holders 804. In certain embodiments the holders each slide into, and lock into, place in the rack, such as with a cam locking mechanism that is recognized as locked audibly and/or physically, or such as with a mechanical key. The rack can be configured so that the holders, when positioned in it, are aligned for proper pipette tip pick-up using an automated liquid dispenser as further described herein.

In certain embodiments, the rack is configured to accept the samples in individual sample tubes 802, each mounted adjacent to a corresponding holder.

The rack can be designed so that it can be easily removed from a dedicated apparatus and carried between the laboratory environment external to the apparatus, such as a bench, and the apparatus. In certain embodiments, the rack is designed to be stable on a horizontal surface, and not easily toppled over during carriage. In certain embodiments the rack has a handle 806 to ease lifting and moving, and the handle can be locked into a vertical position, during carriage, also to reduce risk of the rack being toppled over. The handle has a soft grip 808 in its middle, and is attached to a metallic base member 810 having 4 feet that also serve as position locators when inserting the rack into a dedicated apparatus. The portion of the rack 812 that accepts the samples and holders can be made of plastic, and comprises 12 slots, and may be disposable.

In certain embodiments, the interior of the rack around the location of process tubes in the various holders is configured to have clearance for a heater assembly and/or a magnetic separator as further described herein. For example, the rack is configured so that process tubes on the individual holders are accepted by heater units in a heater assembly as further described in U.S. provisional patent application Ser. No. 60/959,437, filed Jul. 13, 2007.

Still other embodiments of a rack are described in U.S. patent application Ser. No. 12/178,584, filed Jul. 23, 2008.

Liquid Dispenser

Additionally, the holders herein are configured to accept pipette operations both performed manually by an operator, and by an automated pipette head. An exemplary automated pipette head is described in U.S. provisional application Ser. No. 60/959,437, filed Jul. 13, 2007, and incorporated herein by reference in its entirety. Typical features of an automated pipette head suitable for operating with holders as described herein include at least: an ability to pick up pipette tips from the one or more sockets, and to return pipette tips to such sockets after use; to strip and discard a pipette tip from a pipette head after use or upon encountering an error; move a pipette tip with precision from one location of a given holder to another so that, for example, liquid reagents can be located and added to solid reagents to make up solutions, and various liquid reagents can be mixed with one another during a sample preparation protocol. Furthermore, it is desirable that such an automated pipette device can operate on several, such as 2, 3, 4, or 6, holders simultaneously, and thereby perform certain operations in parallel. Thus the pipette head should move in three degrees of freedom.

Heater Assembly & Magnetic Separator

Figure 10:
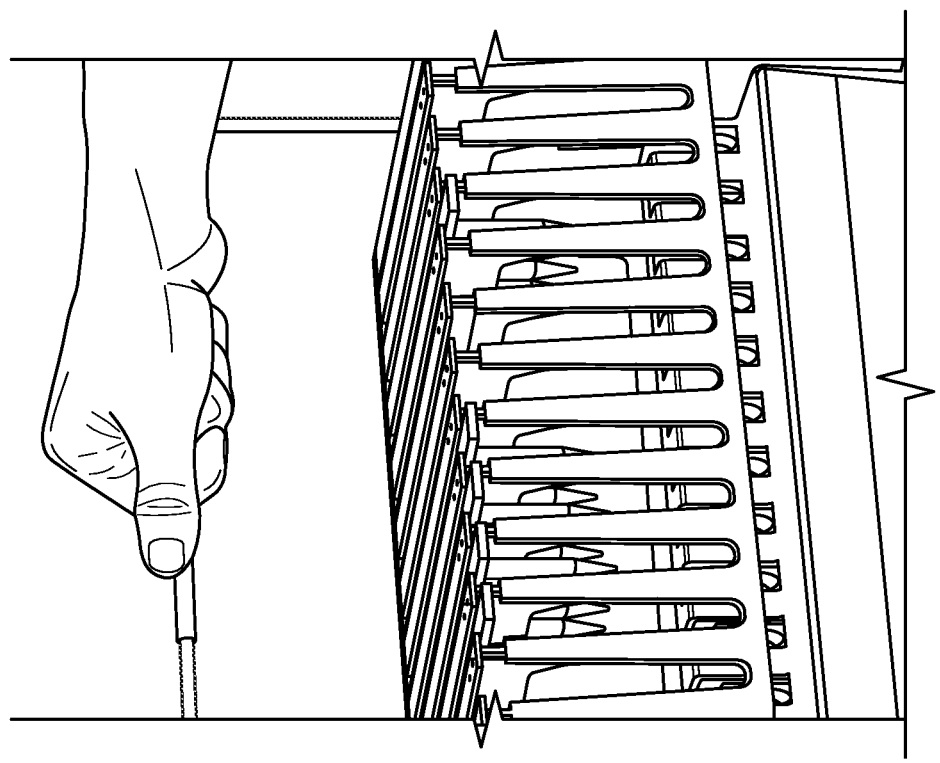
FIG. 10 shows a process tube heating unit, as used in conjunction with a rack.
Figure 10:
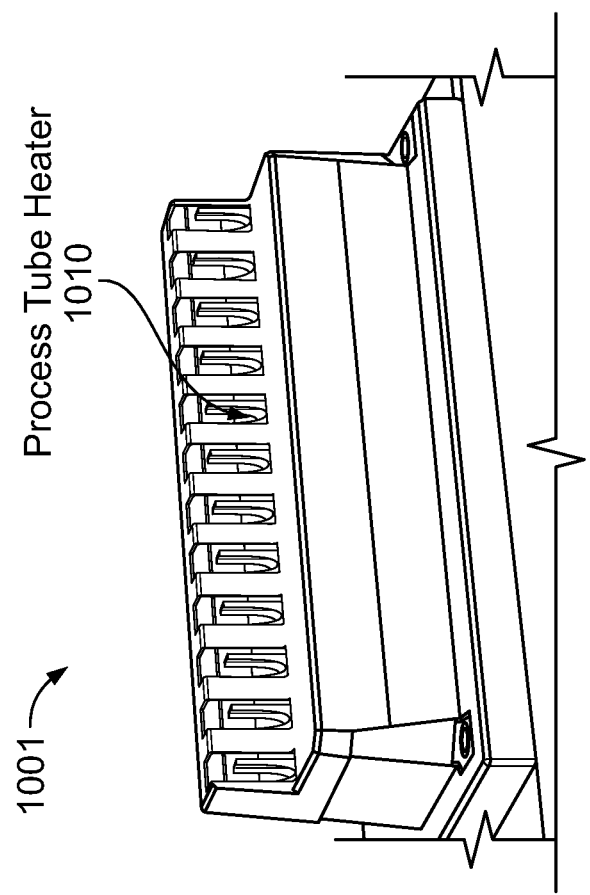

Furthermore, the holders herein are configured so that the process tube is heated by a dedicated heating unit 1001, for example situated in an apparatus for carrying out sample preparation on multiple samples in parallel, as shown in FIG. 10. Typically such a heater assembly comprises one or more independently controllable heater units 1010, each of which comprises a heat block configured to heat a process tube in a holder. In one embodiment, a heat element is a power resistor. The right hand panel of FIG. 10 shows how holders loaded in a rack can be positioned in close proximity to a dedicated heating unit.

Yet additionally, the holders herein are configured so that the process tube is in close enough proximity to a magnetic assembly that separation of magnetic particles from reagents in solution in the process tube can be accomplished. An exemplary magnetic separator is configured to move one or more magnets relative to the one or more process tubes. Typically, the magnet is mounted in such a way that it can be moved in proximity to the process tubes, either in an automated fashion such as under control of a processor, or manually. The magnet can be made of neodymium (e.g., from K &J Magnetics, Inc.) and can have a magnetic strength of 5,000-15000 Gauss (Brmax). The poles of the magnets can be arranged such that one pole faces the heat blocks and the other faces away from the heat blocks.

Advantageously, the heater assembly and magnetic separator operate together to permit successive heating and separation operations to be performed on liquid materials in the one or more process tubes without transporting either the liquid materials or the process tubes to different locations to perform either heating or separation. An exemplary heater assembly and magnetic separator are further described in U.S. provisional patent application Ser. No. 60/959,437, filed Jul. 13, 2007, and incorporated herein by reference in its entirety.

Apparatus Overview

Figure 11:
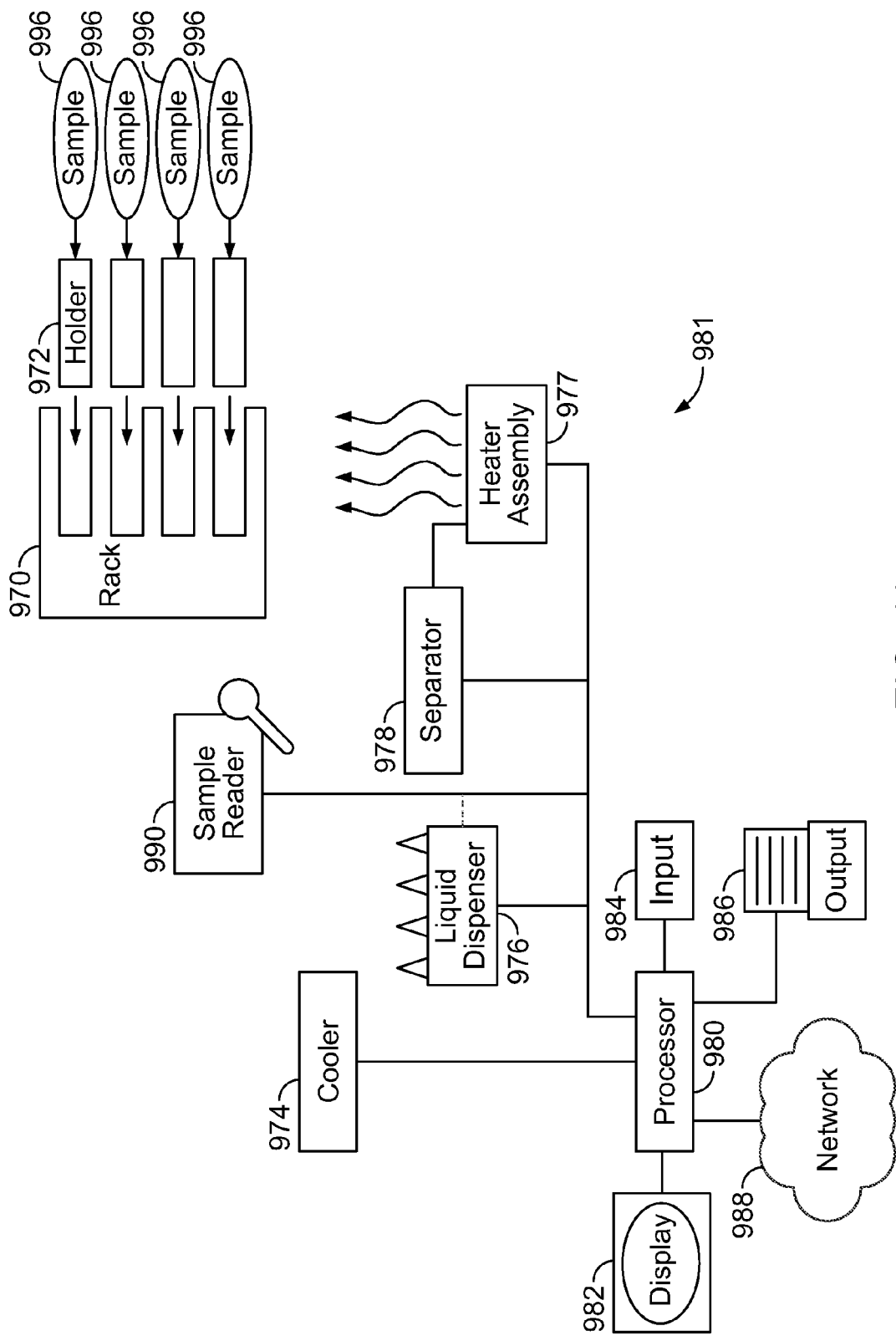
FIG. 11 shows a schematic of an automated apparatus configured to carry out sample preparation using a holder as described herein.

A schematic overview of an apparatus 981 for carrying out automated sample preparation on multiple samples in parallel, according to steps exemplified elsewhere herein, is shown in FIG. 11. The geometric arrangement of the components of system 981 is exemplary and not intended to be limiting.

A processor 980, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 980 can be configured to receive data about a sample to be analyzed, e.g., from a sample reader 990, which may be a barcode reader, an optical character reader, or an RFID scanner (radio frequency tag reader). Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another. Processor 980 can be optionally further configured to transmit results of an analysis to an output device 986 such as a printer, a visual display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIGS. 1A and 1B, the apparatus 981 is configured to operate in conjunction with a complementary rack 970. The rack is itself configured, as further described herein, to receive a number of biological samples 996 in a form suitable for work-up and diagnostic analysis, and a number of holders 972—as further described herein, such as in connection with FIGS. 1A, 1B, 2, and 3A-C, that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly can be controlled by the processor 980. Heater assembly 977 operates in conjunction with a separator 978, such as a magnetic separator, that also can be controlled by processor 980 to move into and out of close proximity to one or more processing chambers associated with the holders 972, wherein particles such as magnetic particles are present.

Liquid dispenser 976, which similarly can be controlled by processor 980, is configured to carry out various suck and dispense operations on respective sample, fluids and reagents in the holders 972, to achieve extraction of nucleic acid from the samples. Liquid dispenser 976 can carry out such operations on multiple holders simultaneously. Sample reader 990 is configured to transmit identifying indicia about the sample, and in some instances the holder, to processor 980. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 976 is also configured to take aliquots of fluid containing nucleic acid extracted from one or more samples and direct them to storage area 974, which may be a cooler. Area 974 contains, for example, a PCR tube corresponding to each sample.

Embodiments of the apparatus shown in outline in FIG. 11, as with other exemplary embodiments described herein, are advantageous because they do not require locations within the apparatus suitably configured for storage of reagents. Therefore, the apparatus in FIG. 11 is self-contained and operates in conjunction with holders 972, wherein the holders are pre-packaged with reagents, such as in locations within it dedicated to reagent storage.

The apparatus of FIG. 11 may be configured to carry out operation in a single location, such as a laboratory setting, or may be portable so that they can accompany, e.g., a physician, or other healthcare professional, who may visit patients at different locations. The apparatus is typically provided with a power-cord so that they can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 11 may further be configured, in other embodiments, for multiplexed sample analysis and/or analysis of multiple batches of samples, where, e.g., a single rack holds a single batch of samples. Each component shown in FIG. 11 may therefore be present as many times as there are batches of samples, though the various components may be configured in a common housing.

EXAMPLES

Example 1: Reagent Holder

An exemplary reagent holder consistent with the description herein has the following dimensions and capacities:
  180 mm long×22 mm wide×100 mm tall;
  Made from Polypropylene.
  One snapped-in low binding 1.7 ml tube that functions as a process tube.
  3 built-in tubes that function as receptacles for reagents, as follows:
    One tube containing 200-1000 μl of wash buffer (0.1 mM Tris, pH 8).
    One tube containing 200-1000 μl of release solution (40 mM NaOH).
    One tube containing 200-1000 μl of neutralization solution (330 mM Tris, pH 8.0).
  One built-in tube that functions as a waste chamber (will hold ~4 ml of liquid waste).
  3 receptacles to accept containers for solid reagents. Snap-in 0.3 ml or 0.65 ml PCR tubes (which are typically stored separately from the reagent holder) are placed in each of these locations, and contain, respectively:
    lyophilized sample preparation reagents (lysis enzyme mix and magnetic affinity beads).
    First lyophilized PCR master mix, probes and primers for a first target analyte detection.
    Second lyophilized PCR master mix, probes and primers for a second target analyte detection (only offered in select cases, such as detection of Chlamydia and Gonorrhea from urine).
  4 pipette tips located in 4 respective sockets.
  Pipette tip Sheath: The pipette tips have a sheath/drip tray underneath to help capture any drip from the pipette tips after being used, and also to prevent unwanted contamination of the instrument.
  Handle and Flex-Lock allows easy insertion, removal, and positive location of strip in rack.
  One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 2: Disposable Reagent Holder Manufacturing

Simple fixtures can be designed and machined to enable handling and processing of multiple strips. There are five steps that can be performed to produce this component. The disposable reagent holder will be placed in a fixture and filled with liquids using manual/electric-multiple pipetting. Immediately after dispensing all liquids into the strip, foil will be heat sealed to the plastic using exemplary heat seal equipment (Hix FH-3000-D Flat Head Press) and the foil trimmed as required. After heat sealing liquids on board, all pellets in tubes can be snapped into the strip, pipette tips can be inserted in their respective sockets, and a barcode label can be affixed. Desiccant packs can be placed into the blow molded or thermoformed rack designed to house 12 holders. Twelve disposable strips will be loaded into the rack and then sealed with foil. The sealed bag will be placed into a carton and labeled for shipping.

Example 3: Foil-Sealing of Buffer Containing Reagent Tubes

Tubes containing buffers have to be sealed with high moisture vapor barrier materials in order to retain the liquid over a long period of time. Disposable holders may need to have a shelf life of 1-2 years, and as such, they should not lose more than say 10-15% of the liquid volume over the time period, to maintain required volume of liquid, and to maintain the concentration of various molecules present in the solution. Moreover, the materials used for construction of the tube as well as the sealing laminate should not react with the liquid buffer. Special plastic laminates may provide the moisture barrier but they may have to be very thick (more than 300 µm thick), causing the piercing force to go up tremendously, or of special, expensive polymer (such as Aclar). Aluminum foils, even a thin foil of a few hundred angstrom provides an effective moisture barrier but bare aluminum reacts with some liquid buffers, such as sodium hydroxide, even an aluminum foil with a sprayed coating of a non-reactive polymer may not be able to withstand the corrosive vapors over a long time. They may react through tiny pin holes present in the coating and may fail as a barrier over time.

For these reasons, aluminum foils with a laminate structure have been identified as a suitable barrier, exemplary properties of which are described below:
1. Sealing
Heat seals to unitized polypropylene strip (sealing temp ~170-180° C.)
No wrinkling, cracking and crazing of the foil after sealing
2. Moisture Vapor Transmission Rate (MVTR)
Loss of less than 10% liquid (20 microliters from a volume of 200 microliter) for a period of 1 year stored at ambient temperature and pressure. (effective area of transport is ~63 $mm^2$); Approximate MVTR 0.8 $cc/m^2$/day
3. Chemistry
Ability to not react with 40 mM Sodium Hydroxide (pH<12.6): foil should have a plastic laminate at least 15 microns thick closer to the sealed fluid.
Ability to not react with other buffers containing mild detergents
4. Puncture
Ability to puncture using a p1000 pipette with a force less than 3 lb
Before puncturing, a fully supported membrane 8 mm in diameter will not stretch more than 5 mm in the orthogonal direction
After puncturing, the foil should not seal the pipette tip around the circumference of the pipette.
5. Other Features
Pin-hole free
No bubbles in case of multi-laminate structures.

Example 4: Mechanism of Piercing Through a Plasticized Laminate and Withdrawing Liquid Buffer The aluminum laminate containing a plastic film described elsewhere herein serves well for not reacting with corrosive reagents such as buffers containing NaOH, and having the favorable properties of pierceability and acting as a moisture barrier. However, it presents some additional difficulties during piercing. The aluminum foil tends to burst into an irregular polygonal pattern bigger than the diameter of the pipette, whereas the plastic film tends to wrap around the pipette tip with minimal gap between the pipette and the plastic film. The diameter of the hole in the plastic film is similar to the maximum diameter of the pipette that had crossed through the laminate. This wrapping of the pipette causes difficulty in dispensing and pipetting operations unless there is a vent hole allowing pressures to equilibrate between outside of the tube and the air inside of the tube.

A strategy for successful pipetting of fluid is as follows:
1. Pierce through the laminate structure and have the pipette go close to the bottom of the reagent tube so that the hole created in the laminate is almost as big as the maximum diameter of the pipette (e.g., ~6 mm for a p1000 pipette)
2. Withdraw the pipette up a short distance so that a small annular vent hole is left between the pipette and the laminate. The p1000 pipette has a smallest outer diameter of 1 mm and maximum outer diameter of 6 mm and the conical section of the pipette is about 28 mm long. A vent hole thickness of a hundred microns is enough to create a reliable vent hole. This corresponds to the pipette inserted to a diameter of 5.8 mm, leaving an annulus of 0.1 mm around it.
3. Withdraw fluid from the tube. Note that the tube is designed to hold more fluid than is necessary to withdraw from it for a sample preparation procedure.

Example 5: Foil Piercing and Dissolution of Lyophilized Reagents

The containers of lyophilized reagents provided in conjunction with a holder as described herein are typically sealed by a non-plasticized aluminum foil (i.e., not a laminate as is used to seal the reagent tubes). Aluminum foil bursts into an irregular polygonal pattern when pierced through a pipette and leaves an air vent even though the pipette is moved to the bottom of the tube. In order to save on reagents, it is desirable to dissolve the reagents and maximize the amount withdrawn from the tube. To accomplish this, a star-ridged (stellated) pattern is placed at the bottom of the container to maximize liquid volume withdrawn, and flow velocity in between the ridges.

Exemplary steps for dissolving and withdrawing fluid are as follows:
1. Pierce through the pipette and dispense the fluid away from the lyophilized material. If the pipette goes below the level of the lyophilized material, it will go into the pipette and may cause jamming of the liquid flow out of the pipette.
2. Let the lyophilized material dissolve for a few seconds.
3. Move pipette down touching the ridged-bottom of the tube
4. Perform an adequate number of suck and spit operations (4-10) to thoroughly mix the reagents with the liquid buffer.
5. Withdraw all the reagents and move pipette to dispense it into the next processing tube.

Example 6: Material and Surface Property of the Lysis Tube

The material, surface properties, surface finish has a profound impact on the sensitivity of the assay performed. In clinical applications, DNA/RNA as low as 50 copies/sample (~1 ml volume) need to be positively detected in a background of billions of other molecules, some of which strongly inhibit PCR. In order to achieve these high level of sensitivities, the surface of the reaction tube as well as the material of the surface has to be chosen to have minimal binding of polynucleotides. During the creation of the injection molding tool to create these plastic tubes, the inherent surfaces created by machining may have large surface area due to cutting marks as large as tens of microns of peaks and valleys. These surfaces have to be polished to SPI A1/A2 finish (mirror finish) to remove the microscopic surface irregularities. Moreover, the presence of these microscopic valleys will trap magnetic beads (0.5-2µ) at unintended places and cause irregular performance. In addition to actual surface roughness, the surface hydrophobicity/surface molecules present may cause polynucleotides to stick at unintended places and reduce sensitivity of the overall test. In addition to the base material uses, such as homogenous polupropylene and other polymers, specific materials used during the molding of these tubes, such as mold release compounds or any additives to aid in the fabrication can have a profound impact on the performance of the reactions.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. A unitized reagent holder and reagent system, comprising:
   a strip, to which is attached:
   a single process tube;
   at least three reagent tubes;
   a sample lysis reagent in a first said reagent tube;
   a PCR reagent for a first analyte in a second said reagent tube;
   one or more liquid reagents in a third said reagent tube; and
   two or more sockets holding two or more pipette tips, wherein the ratio of sockets holding pipette tips to process tubes is at least two.

2. The unitized reagent holder of claim 1, further comprising a laminate that seals closed an inlet of each of the containers.

3. The unitized reagent holder of claim 1, wherein at least one of the containers is removable.

4. The unitized reagent holder of claim 1, further comprising a pipette tip sheath configured to surround one of the pipette tips.

5. The unitized reagent holder of claim 1, further comprising a waste tube attached to the strip.

6. A reagent holder and reagent system comprising:
   a single process tube;
   at least three reagent tubes;
   a sample lysis reagent in a first said reagent tube;
   a PCR reagent in a second said reagent tube;
   one or more liquid reagents in a third said reagent tube;
   two or more sockets holding pipette tips, wherein the ratio of sockets holding pipette tips to process tubes is at least two; and
   wherein the process tube, the two or more sockets configured to hold pipette tips, and the reagent tubes are all joined to a single connecting member.

7. The reagent holder and reagent system of claim 6, further comprising:
   a waste tube; and
   a pipette tip sheath configured to surround at least one of the pipette tips.

8. The reagent holder and reagent system of claim 6, wherein the connecting member has a first end and a second end, and the process tube is located at either of the first or second ends.

9. The unitized reagent holder of claim 1, wherein one of the containers holds a release solution.

* * * * *